US010896324B2

United States Patent
Shudo et al.

(10) Patent No.: US 10,896,324 B2
(45) Date of Patent: Jan. 19, 2021

(54) LINE-OF-SIGHT DETECTION DEVICE AND METHOD FOR DETECTING LINE OF SIGHT

(71) Applicant: JVC KENWOOD Corporation, Yokohama (JP)

(72) Inventors: Katsuyuki Shudo, Yokohama (JP); Shuji Hakoshima, Yokohama (JP)

(73) Assignee: JVC KENWOOD Corporation, Yokohama (JP)

(*) Notice: Subject to any disclaimer, the term of this patent is extended or adjusted under 35 U.S.C. 154(b) by 0 days.

(21) Appl. No.: 16/249,988

(22) Filed: Jan. 17, 2019

(65) Prior Publication Data

US 2019/0147241 A1 May 16, 2019

Related U.S. Application Data

(63) Continuation of application No. PCT/JP2017/022594, filed on Jun. 19, 2017.

(30) Foreign Application Priority Data

Aug. 24, 2016 (JP) .................... 2016-163556

(51) Int. Cl.
*H04N 5/235* (2006.01)
*G06K 9/00* (2006.01)
(Continued)

(52) U.S. Cl.
CPC .......... *G06K 9/00604* (2013.01); *A61B 3/113* (2013.01); *G06K 9/0061* (2013.01);
(Continued)

(58) Field of Classification Search
CPC ............... A61B 3/113; G06K 9/00255; G06K 9/00604; G06K 9/0061; G06T 1/00;
(Continued)

(56) References Cited

U.S. PATENT DOCUMENTS 6,850,631 B1  2/2005 Oda et al.
2006/0017887 A1* 1/2006 Jacobson ............... G03B 21/30
                                                   353/30
(Continued)

FOREIGN PATENT DOCUMENTS

JP  2000-207536  7/2000
JP  2005-185431  7/2005
(Continued)

OTHER PUBLICATIONS

International Search Report and Written Opinion for International Patent Application No. PCT/JP2017/022594 dated Sep. 12, 2017, 9 pages.

(Continued)

*Primary Examiner* — Md N Haque
(74) *Attorney, Agent, or Firm* — Amin, Turocy & Watson, LLP

(57) ABSTRACT

A line-of-sight detection device includes an image data acquisition unit that acquires image data of a face of a subject irradiated with detection light emitted from at least one light source, a line-of-sight detection unit that detects a line of sight of the subject based on the image data, an image processing unit that performs image processing on the image data to generate a feature image of the face and an eyeglasses reflection image indicating a reflection image of the at least one light source on eyeglasses worn on the face, and a display controller that causes a display device to display the feature image and the eyeglasses reflection image in a different display form in a composite image in which the feature image and the eyeglasses reflection image are combined.

9 Claims, 19 Drawing Sheets

(51) Int. Cl.
    *A61B 3/113*     (2006.01)
    *G06T 1/00*     (2006.01)
    *H04N 5/225*     (2006.01)
    *G09G 5/00*     (2006.01)

(52) U.S. Cl.
    CPC ............ *G06K 9/00255* (2013.01); *G06T 1/00* (2013.01); *G09G 5/003* (2013.01); *H04N 5/225* (2013.01); *H04N 5/2353* (2013.01); *G09G 2320/0626* (2013.01); *G09G 2320/0686* (2013.01); *G09G 2340/10* (2013.01)

(58) Field of Classification Search
    CPC ... G09G 2320/0626; G09G 2320/0686; G09G 2340/10; G09G 5/003
    See application file for complete search history.

(56) References Cited

U.S. PATENT DOCUMENTS

| | | | |
|---|---|---|---|
| 2007/0279590 A1 | 12/2007 | Ebisawa | |
| 2009/0102845 A1* | 4/2009 | Takemoto | G06K 9/00375 345/426 |
| 2010/0254571 A1* | 10/2010 | Matsuura | G06K 9/3266 382/103 |
| 2015/0085250 A1* | 3/2015 | Larsen | A61B 3/0025 351/206 |
| 2015/0161472 A1* | 6/2015 | Yoshioka | G06K 9/0061 382/197 |
| 2015/0355463 A1* | 12/2015 | Sako | G06K 9/00671 345/633 |
| 2016/0270655 A1 | 9/2016 | Caraffi et al. | |

FOREIGN PATENT DOCUMENTS

| | | |
|---|---|---|
| JP | 2005-296382 | 10/2005 |
| JP | 2007-004448 | 1/2007 |
| JP | 2009-254525 | 11/2009 |
| JP | 2010-244156 | 10/2010 |
| WO | 2015086617 | 6/2015 |

OTHER PUBLICATIONS

Extended European Search Report for European Patent Application No. 17843173.0 dated Jul. 8, 2019.

* cited by examiner

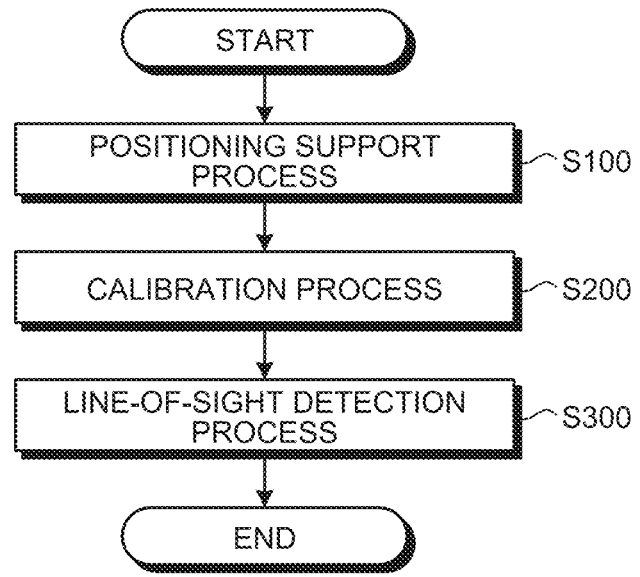
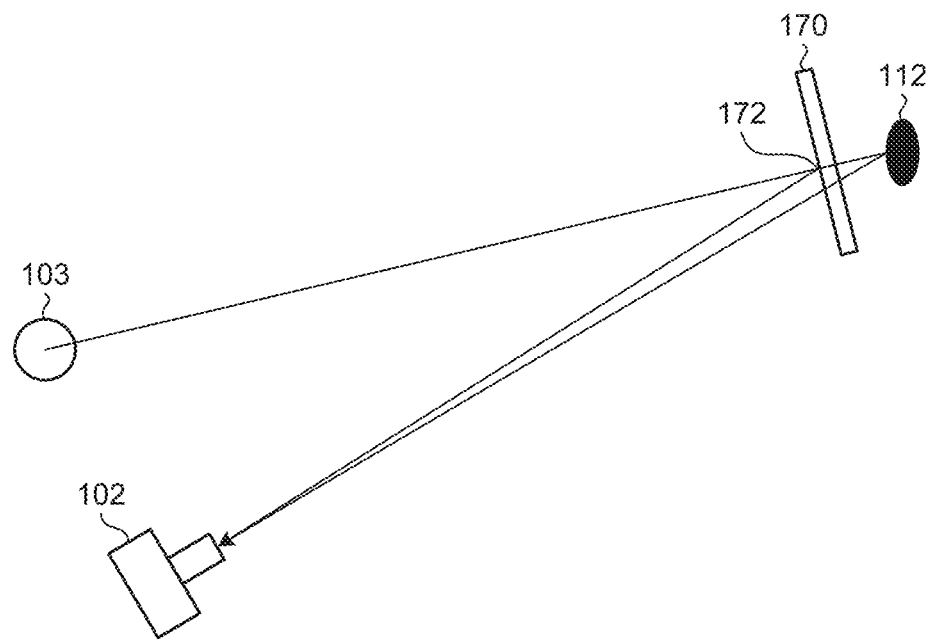

[RAW DATA]

[BINARIZED DATA]

[CONTOUR IMAGE]

[LUMINANCE ADJUSTMENT]

[EYEGLASSES REFLECTION IMAGE]

[COMPOSITE IMAGE]

LINE-OF-SIGHT DETECTION DEVICE AND METHOD FOR DETECTING LINE OF SIGHT

CROSS-REFERENCE TO RELATED APPLICATIONS

This application is a Continuation of PCT International Application No. PCT/JP2017/022594 filed in Japan on Jun. 19, 2017, which claims priority to Japanese Patent Application No. 2016-163556 filed in Japan on Aug. 24, 2016, both of which are hereby incorporated by reference.

FIELD

The present invention relates to a line-of-sight detection device and a method for detecting a line of sight.

BACKGROUND

As a technique for detecting a line of sight, a corneal reflection method has been known. The corneal reflection method is a method for detecting a line of sight of a subject in which the subject is irradiated with infrared light emitted from a light source, an eye of the subject irradiated with the infrared light is captured by a camera, and a position of a pupil with respect to a corneal reflection image, which is a reflection image of a light source on a corneal surface, is detected (for example, see Japanese Laid-open Patent Publication No. 2010-244156 A).

SUMMARY

In a case where the subject is wearing eyeglasses, there is a possibility that the infrared light emitted to the subject is reflected by the eyeglasses. When the infrared light is reflected by the eyeglasses, the detection accuracy of the line of sight may be lowered. For example, in a case where the reflection image of the light source on the eyeglasses and the eye of the subject overlap in the visual field area of the camera, it becomes difficult to detect the corneal reflection image and the pupil. When the corneal reflection image and the pupil are not detected excellently, the detection accuracy of the line of sight of the subject is lowered.

A line-of-sight detection device and a method for detecting a line of sight are disclosed.

According to one aspect, there is provided a line-of-sight detection device, comprising: an image data acquisition unit that acquires image data of a face of a subject irradiated with detection light emitted from a light source; a line-of-sight detection unit that detects a line of sight of the subject based on the image data; an image processing unit that performs image processing on the image data to generate a feature image of the face and an eyeglasses reflection image indicating a reflection image of the light source on eyeglasses worn on the face; and a display controller that causes a display device to display the feature image and the eyeglasses reflection image in a different display form in a composite image in which the feature image and the eyeglasses reflection image are combined.

The above and other objects, features, advantages and technical and industrial significance of this application will be better understood by reading the following detailed description of presently preferred embodiments of the application, when considered in connection with the accompanying drawings.

BRIEF DESCRIPTION OF THE DRAWINGS

FIG. 7 is a flowchart illustrating an example of a method for detecting a line of sight according to the first embodiment.

FIG. 8 is a diagram schematically illustrating a relationship among a pupil of a subject wearing eyeglasses, a stereo camera device, and a light source.

DETAILED DESCRIPTION OF THE PREFERRED EMNODIMENTS

Hereinafter, embodiments of the present invention will be described with reference to the accompanying drawings, but the present invention is not limited thereto. Constituent elements of the embodiments described below may be appropriately combined. In addition, some constituent elements may not be used.

In the following descriptions, a positional relationship between respective parts will be described by setting a three-dimensional global coordinate system. A direction parallel to an X axis of a predetermined plane is defined as an X-axis direction, a direction parallel to a Y axis of the predetermined plane orthogonal to the X axis is defined as a Y-axis direction, and a direction parallel to a Z axis orthogonal to each of the X axis and the Y axis is defined as a Z-axis direction. The predetermined plane includes an XY plane.

First Embodiment

Figure 1:
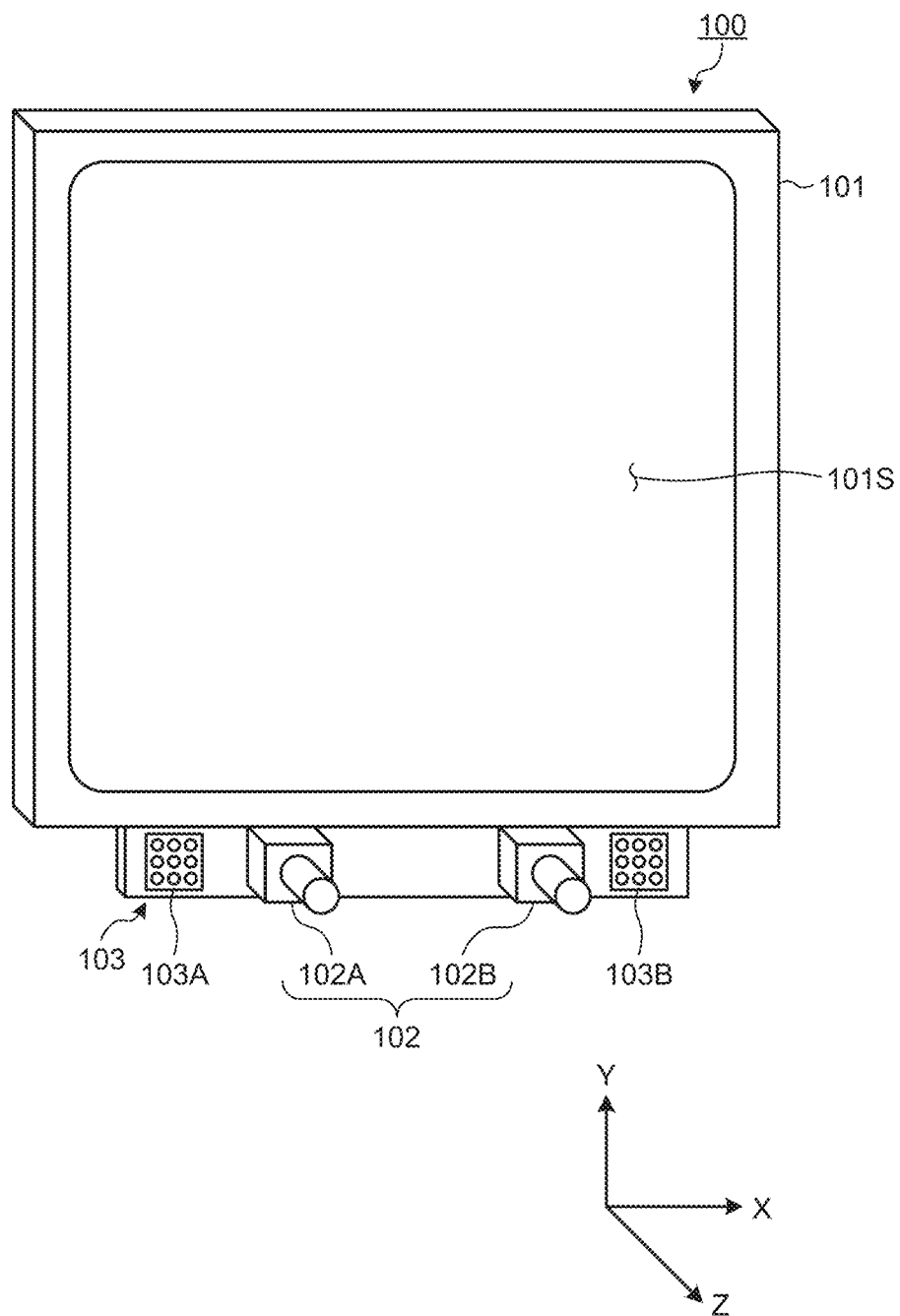
FIG. 1 is a perspective view schematically illustrating an exemplary line-of-sight detection device according to a first embodiment.

A first embodiment will be described. FIG. 1 is a perspective view schematically illustrating an exemplary line-of-sight detection device 100 according to the present embodiment. The line-of-sight detection device 100 is used for, for example, a diagnostic support apparatus for supporting diagnosis of developmental disorder.

[Overview of Line-of-Sight Detection Device]

As illustrated in FIG. 1, the line-of-sight detection device 100 includes a display device 101, a stereo camera device 102, and a light source 103.

The display device 101 includes a flat panel display such as a liquid crystal display (LCD) and an organic electroluminescence display (OELD).

In the present embodiment, a display screen 101S of the display device 101 is substantially parallel to the XY plane. The X-axis direction is a horizontal direction of the display screen 101S, the Y-axis direction is a vertical direction of the display screen 101S, and the Z-axis direction is a depth direction orthogonal to the display screen 101S.

The stereo camera device 102 takes an image of a subject and obtains image data of the subject. The stereo camera device 102 includes a first camera 102A and a second camera 102B, which are disposed at different positions. The stereo camera device 102 is disposed below the display screen 101S of the display device 101. The first camera 102A and the second camera 102B are disposed in the X-axis direction. The first camera 102A is disposed in the −X direction with respect to the second camera 102B. Each of the first camera 102A and the second camera 102B includes an infrared camera, and has, for example, an optical system capable of transmitting near-infrared light with a wavelength of 850 nm and an imaging element capable of receiving the near-infrared light.

The light source 103 emits detection light. The light source 103 includes a first light source 103A and a second light source 103B, which are disposed at different positions. The light source 103 is disposed below the display screen 101S of the display device 101. The first light source 103A and the second light source 103B are disposed in the X-axis direction. The first light source 103A is disposed in the −X direction with respect to the first camera 102A. The second light source 103B is disposed in the +X direction with respect to the second camera 102B. Each of the first light source 103A and the second light source 103B includes a light emitting diode (LED), and is capable of emitting near-infrared light with a wavelength of 850 nm, for example. Note that the first light source 103A and the second light source 103B may be disposed between the first camera 102A and the second camera 102B.

Figure 2:
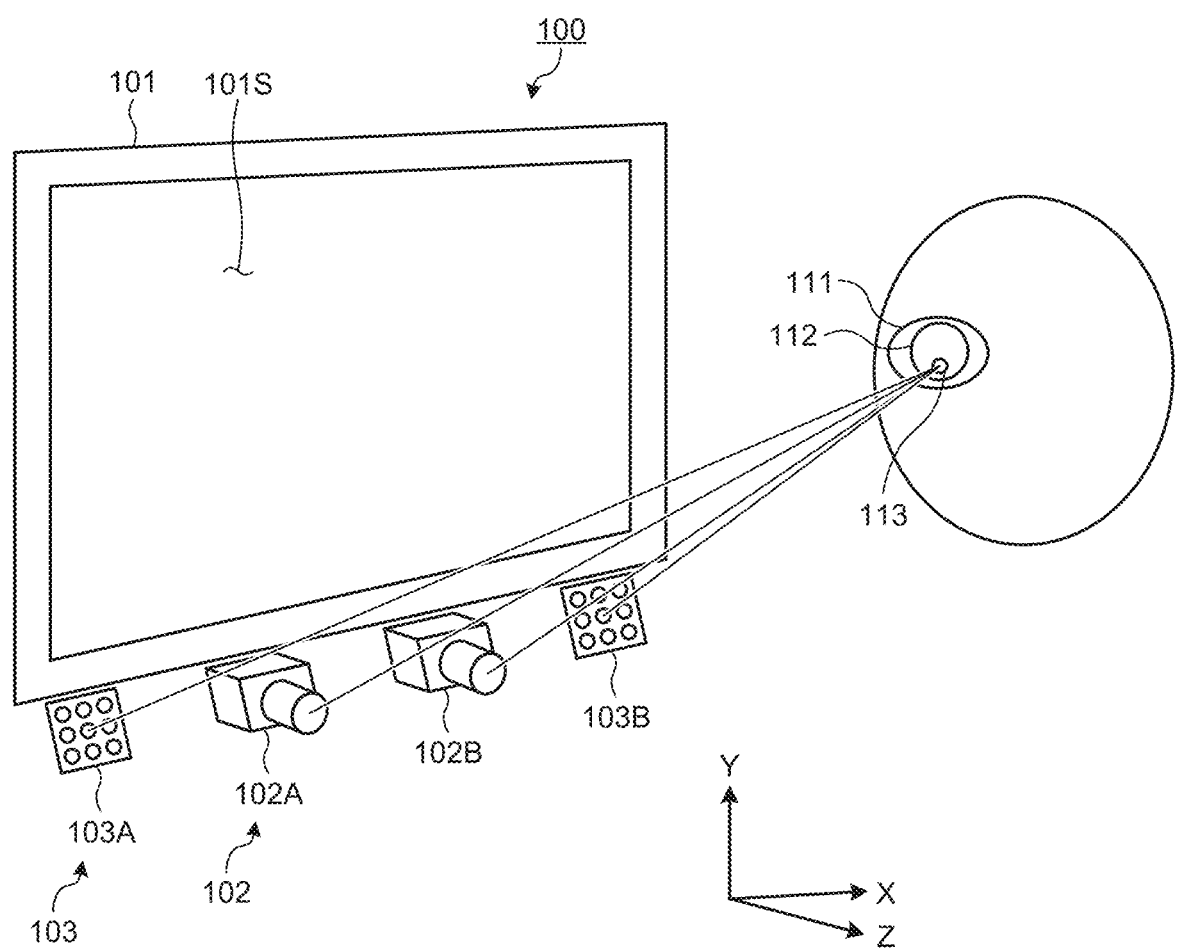
FIG. 2 is a diagram schematically illustrating a positional relationship among a display device, a stereo camera device, a light source, and an eyeball of a subject according to the first embodiment.

FIG. 2 is a diagram schematically illustrating a positional relationship among the display device 101, the stereo camera device 102, the light source 103, and an eyeball 111 of the subject according to the present embodiment.

The light source 103 emits infrared light as detection light to illuminate the eyeball 111 of the subject. The stereo camera device 102 takes an image of the eyeball 111 with the second camera 102B when the eyeball 111 is irradiated with the detection light emitted from the first light source 103A, and takes an image of the eyeball 111 with the first camera 102A when the eyeball 111 is irradiated with the detection light emitted from the second light source 103B.

A frame synchronous signal is output from at least one of the first camera 102A and the second camera 102B. The first light source 103A and the second light source 103B emit the detection light based on the frame synchronous signal. When the eyeball 111 is irradiated with the detection light emitted from the second light source 103B, the first camera 102A obtains image data of the eyeball 111. When the eyeball 111 is irradiated with the detection light emitted from the first light source 103A, the second camera 102B obtains image data of the eyeball 111.

When the eyeball 111 is irradiated with the detection light, a part of the detection light is reflected by a pupil 112. The light reflected by the pupil 112 enters the stereo camera device 102. Further, when the eyeball 111 is irradiated with the detection light, a corneal reflection image 113 is formed on the eyeball 111. The corneal reflection image 113 is a reflection image of the light source 103 on a corneal surface. The light from the corneal reflection image 113 enters the stereo camera device 102.

By appropriately setting relative positions of the first camera 102A, the second camera 102B, the first light source 103A, and the second light source 103B, an intensity of the light entering the stereo camera device 102 from the pupil 112 decreases, and an intensity of the light entering the stereo camera device 102 from the corneal reflection image 113 increases. That is, the image of the pupil 112 obtained by the stereo camera device 102 has low luminance, and the image of the corneal reflection image 113 has high luminance. The stereo camera device 102 can detect a position of the pupil 112 and a position of the corneal reflection image 113 based on the luminance of the obtained images.

[Hardware Configuration]

Figure 3:
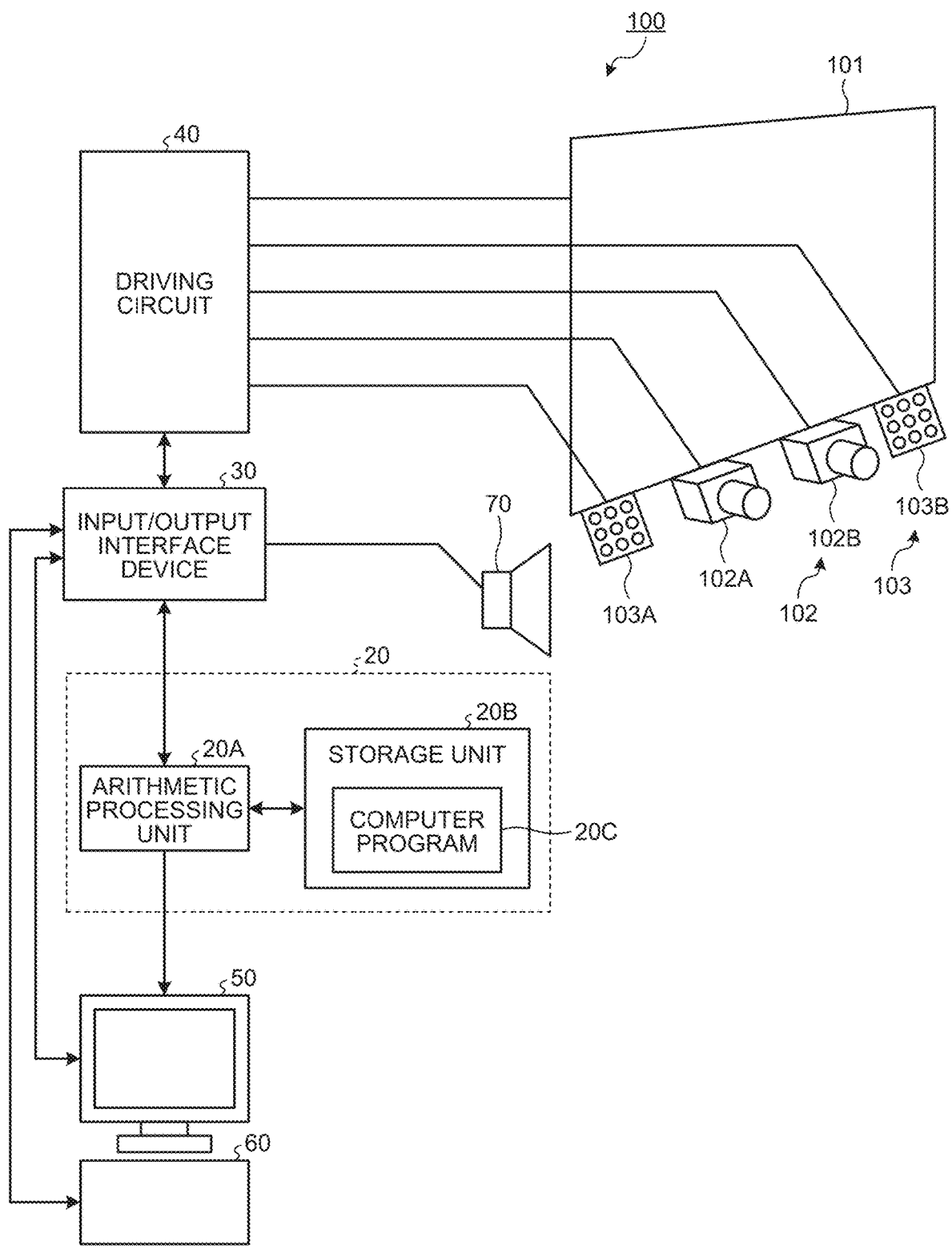
FIG. 3 is a diagram illustrating an exemplary hardware configuration of the line-of-sight detection device according to the first embodiment.

FIG. 3 is a diagram illustrating an exemplary hardware configuration of the line-of-sight detection device 100 according to the present embodiment. As illustrated in FIG. 3, the line-of-sight detection device 100 includes the display device 101, the stereo camera device 102, the light source 103, a computer system 20, an input/output interface device 30, a driving circuit 40, an output device 50, an input device 60, and a voice output device 70. The computer system 20 includes an arithmetic processing unit 20A and a storage unit 20B. A computer program 20C is stored in the storage unit 20B.

The computer system 20, the driving circuit 40, the output device 50, the input device 60, and the voice output device 70 perform data communication via the input/output interface device 30.

The arithmetic processing unit 20A includes a microprocessor such as a central processing unit (CPU). The storage unit 20B includes a nonvolatile memory such as a read-only memory (ROM), or a volatile memory such as a random access memory (RAM). The arithmetic processing unit 20A executes arithmetic processing according to the computer program 20C stored in the storage unit 20B.

The driving circuit 40 generates a drive signal, and outputs it to the display device 101, the stereo camera device 102, and the light source 103. Further, the driving circuit 40 supplies the image data of the eyeball 111 obtained by the stereo camera device 102 to the computer system 20 via the input/output interface device 30.

The output device 50 includes a display device such as a flat panel display. Note that the output device 50 may include a printer. The input device 60 generates input data by being operated. The input device 60 includes a keyboard or a mouse for a computer system. Note that the input device 60 may include a touch sensor provided on the display screen of the output device 50 that is the display device. The voice output device 70 includes a speaker, and outputs, for example, voice for calling the subject's attention.

In the present embodiment, the display device 101 and the computer system 20 are separate devices. Note that the display device 101 and the computer system 20 may be integrated. For example, in a case where the line-of-sight detection device 100 includes a tablet personal computer system, the computer system 20, the input/output interface device 30, the driving circuit 40, and the display device 101 may be mounted on the tablet personal computer.

Figure 4:
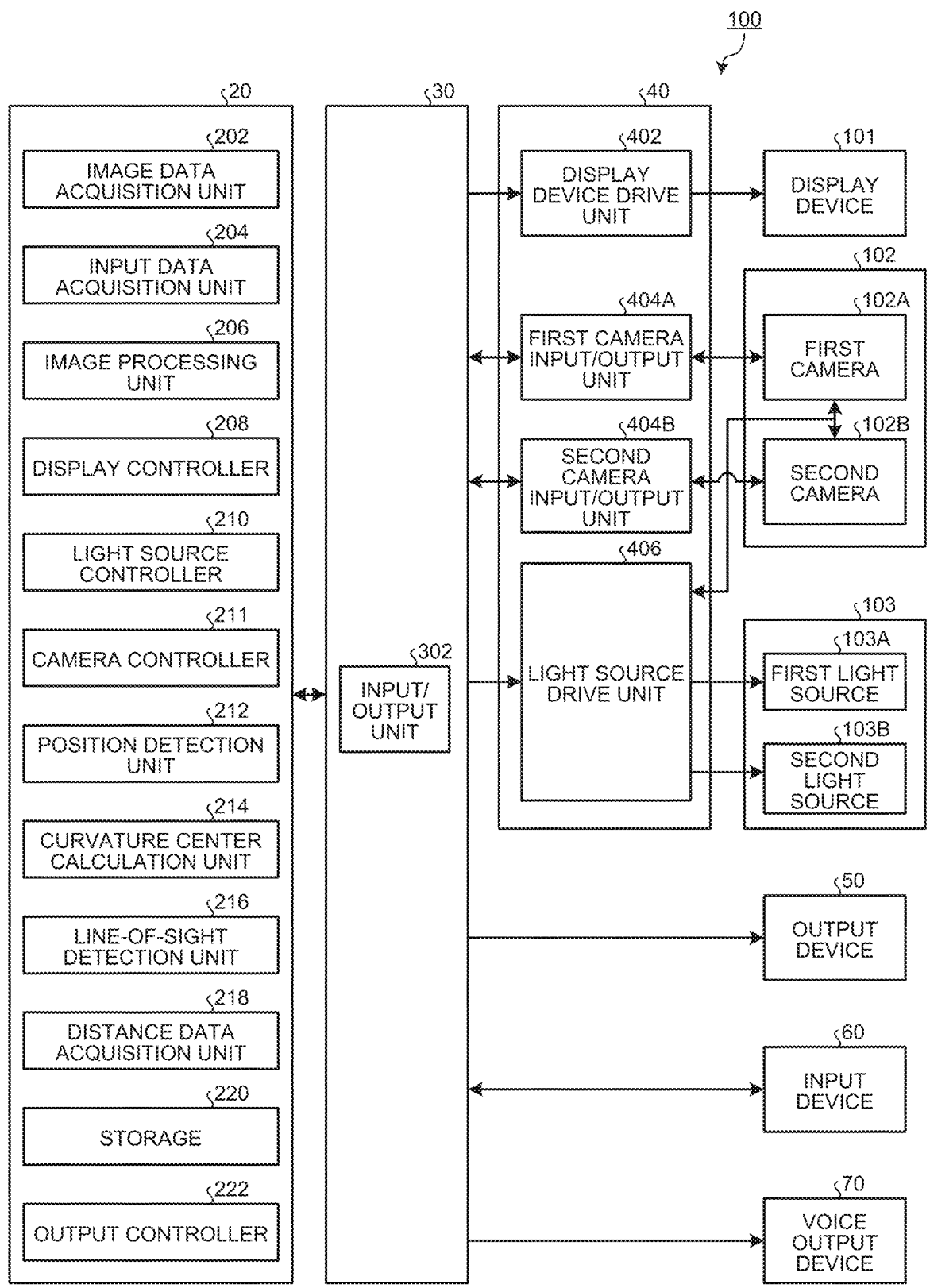
FIG. 4 is a functional block diagram illustrating an example of the line-of-sight detection device according to the first embodiment.

FIG. 4 is a functional block diagram illustrating an example of the line-of-sight detection device 100 according to the present embodiment. As illustrated in FIG. 4, the input/output interface device 30 includes an input/output unit 302. The driving circuit 40 includes a display device drive unit 402 that generates a drive signal for driving the display device 101 and outputs it to the display device 101, a first camera input/output unit 404A that generates a drive signal for driving the first camera 102A and outputs it to the first camera 102A, a second camera input/output unit 404B that generates a drive signal for driving the second camera 102B and outputs it to the second camera 102B, and a light source drive unit 406 that generates a drive signal for driving the first light source 103A and the second light source 103B and outputs it to the first light source 103A and the second light source 103B. Further, the first camera input/output unit 404A supplies the image data of the eyeball 111 obtained by the first camera 102A to the computer system 20 via the input/output unit 302. The second camera input/output unit 404B supplies the image data of the eyeball 111 obtained by the second camera 102B to the computer system 20 via the input/output unit 302.

The computer system 20 controls the line-of-sight detection device 100. The computer system 20 includes an image data acquisition unit 202, an input data acquisition unit 204, an image processing unit 206, a display controller 208, a light source controller 210, a camera controller 211, a position detection unit 212, a curvature center calculation unit 214, a line-of-sight detection unit 216, a distance data acquisition unit 218, a storage 220, and an output controller 222. A function of the computer system 20 are performed by the arithmetic processing unit 20A, the storage unit 20B, and the computer program 20C stored in the storage unit 20B.

The image data acquisition unit 202 acquires the image data of a face of the subject captured by the stereo camera device 102 including the first camera 102A and the second camera 102B from the stereo camera device 102 via the input/output unit 302. The image data is digital data. The image data of the face of the subject includes the image data of the eyeball 111. The stereo camera device 102 takes the image of the face of the subject to be irradiated with the detection light emitted from the light source 103. The image data acquisition unit 202 acquires the image data of the face of the subject to be irradiated with the detection light emitted from the light source 103 from the stereo camera device 102 via the input/output unit 302.

The input data acquisition unit 204 acquires the input data generated by the input device 60 being operated from the input device 60 via the input/output unit 302.

The image processing unit 206 performs image processing on the image data acquired by the image data acquisition unit 202. The image processing unit 206 performs the image processing on the image data, and generates a feature image indicating an image of a feature portion within the face of the subject, and generates an eyeglasses reflection image indicating a reflection image of the light source 103 on the eyeglasses worn on the face of the subject.

The display controller 208 causes the display device 101 to display a specific image. In the present embodiment, the display controller 208 causes the display device 101 to display a composite image in which the feature image and the eyeglasses reflection image generated by the image processing unit 206 are combined. The display controller 208 causes the display device 101 to display the feature image and the eyeglasses reflection image in a different display form in the composite image in which the feature image and the eyeglasses reflection image are combined. The display form on the display device 101 includes at least one of luminance, color, lightness, and saturation of the image. In the present embodiment, the display controller 208 causes the display device 101 to display the eyeglasses reflection image in an emphasized manner compared with the feature image. For example, the display controller 208 causes the display device 101 to display the eyeglasses reflection image with luminance higher than that of the feature image in the composite image. Note that the display controller 208 may cause the display device 101 to display the eyeglasses reflection image with lightness higher than that of the feature image or with saturation higher than that of the feature image in the composite image.

The light source controller 210 controls the light source drive unit 406 to control an operating state of the first light source 103A and the second light source 103B. The light source controller 210 controls the first light source 103A and the second light source 103B such that the first light source 103A and the second light source 103B emit the detection light at different timings. Further, the light source controller 210 controls the amount of light of the detection light emitted from the first light source 103A and the amount of light of the detection light emitted from the second light source 103B. The control of the amount of light of the detection light emitted from the first light source 103A includes at least one of control of light emission intensity of the first light source 103A and control of light emission time of the first light source 103A. Likewise, the control of the amount of light of the detection light emitted from the second light source 103B includes at least one of control of light emission intensity of the second light source 103B and control of light emission time of the second light source 103B. In the present embodiment, the light source controller 210 controls the first light source 103A and the second light source 103B such that the amount of light of the detection light emitted from the first light source 103A and the amount of light of the detection light emitted from the second light source 103B become the same amount.

The camera controller 211 controls the first camera input/output unit 404A and the second camera input/output unit 404B to control an operating state of the stereo camera device 102 including the first camera 102A and the second camera 102B. The camera controller 211 controls an exposure value of the detection light in the first camera 102A and an exposure value of the detection light in the second camera 102B. Each of the exposure value of the detection light in the first and second cameras 102A and 102B indicates an exposure amount of the detection light entering the imaging element from the face of the subject illuminated with the detection light via each of an optical system of the first and second cameras 102A and 102B. A control of the exposure value of the detection light in the first and second cameras 102A and 102B includes at least one of a control of a shutter speed of the first and second cameras 102A and 102B and a control of an aperture value of the optical system of the first and second cameras 102A and 102B.

The position detection unit 212 detects positional data of a pupil center based on the image data of the eyeball 111 acquired by the image data acquisition unit 202. Further, the position detection unit 212 detects positional data of a corneal reflection center based on the image data of the eyeball 111 acquired by the image data acquisition unit 202. The pupil center is a center of the pupil 112. The corneal reflection center is a center of the corneal reflection image 113. The position detection unit 212 detects the positional data of the pupil center and the positional data of the corneal reflection center with respect to each of the right and left eyeballs 111 of the subject.

The curvature center calculation unit 214 calculates positional data of a corneal curvature center of the eyeball 111 based on the image data of the eyeball 111 acquired by the image data acquisition unit 202.

The line-of-sight detection unit 216 detects a line of sight of the subject based on the image data of the eyeball 111 acquired by the image data acquisition unit 202. The line of sight of the subject includes a line-of-sight vector indicating a line-of-sight direction being observed by the subject. The line-of-sight detection unit 216 detects line-of-sight vectors of the right and left eyeballs 111 of the subject based on the positional data of the pupil center and the positional data of the corneal curvature center obtained from the image data of the eyeball 111.

Further, the line-of-sight detection unit 216 detects positional data of a gaze point of the subject based on the detected line-of-sight vector. In the present embodiment, the gaze point of the subject includes an intersection point of the line-of-sight vector of the subject and the display screen 101S of the display device 101. In the present embodiment, the positional data of the gaze point indicates positional data of the intersection point of the line-of-sight vector of the subject defined in the global coordinate system and the display screen 101S of the display device 101.

The distance data acquisition unit 218 obtains distance data between the display screen 101S of the display device 101 and the face of the subject. The distance data acquisition unit 218 detects distance data based on the positional data of the pupil center detected by the position detection unit 212. The positional data of the pupil center in the global coordinate system is detected, whereby a distance between the center of the display screen 101S of the display device 101 and the eyeball 111 of the subject is calculated. The distance data acquisition unit 218 obtains the distance between the center of the display screen 101S of the display device 101 and the eyeball 111 of the subject as the distance data between the display screen 101S of the display device 101 and the face of the subject.

The storage 220 stores the computer program 20C and various data.

The output controller 222 outputs data to at least one of the display device 101, the output device 50, and the voice output device 70. For example, the output controller 222 causes the display device 101 or the output device 50 to display the positional data of the gaze point of each of the right and left eyeballs 111 of the subject.

[Principle of Line-of-Sight Detection]

Next, a principle of line-of-sight detection according to the present embodiment will be described. In the following descriptions, the outline of processing performed by the curvature center calculation unit 214 will be mainly described. The curvature center calculation unit 214 calculates the positional data of the corneal curvature center of the eyeball 111 based on the image data of the eyeball 111.

Figure 5:
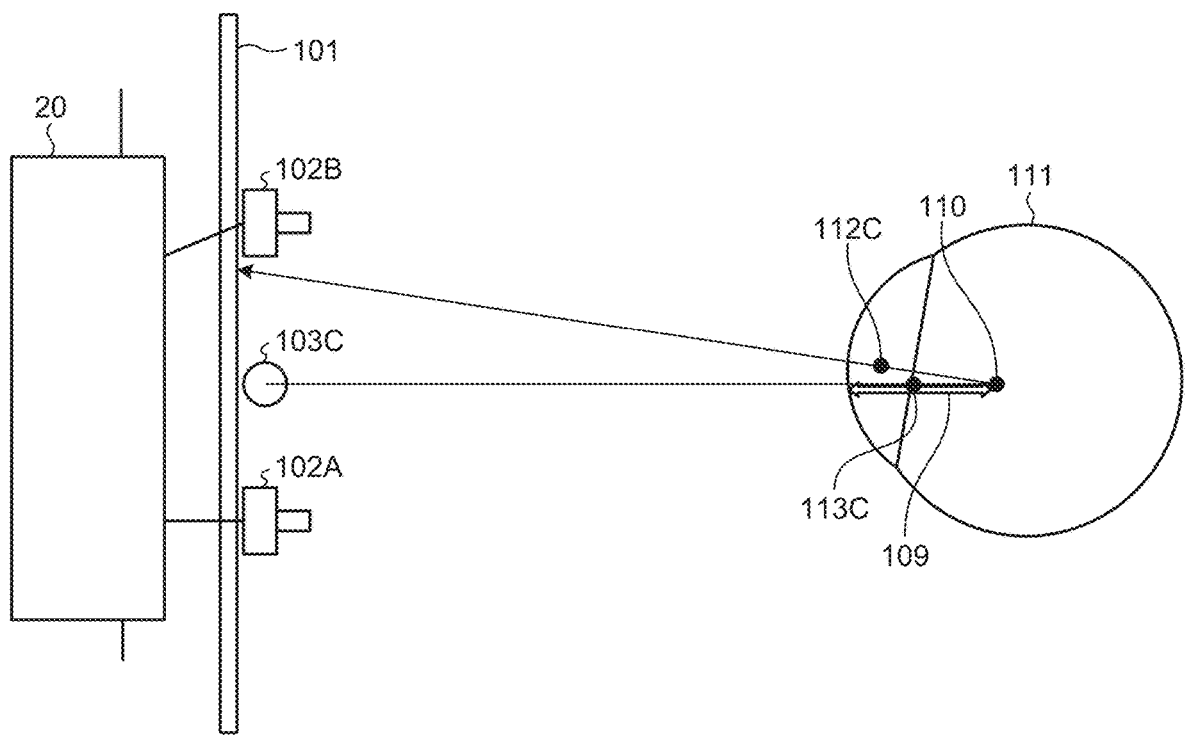
FIG. 5 is a schematic diagram for illustrating a method for calculating positional data of a corneal curvature center according to the first embodiment.
Figure 6:
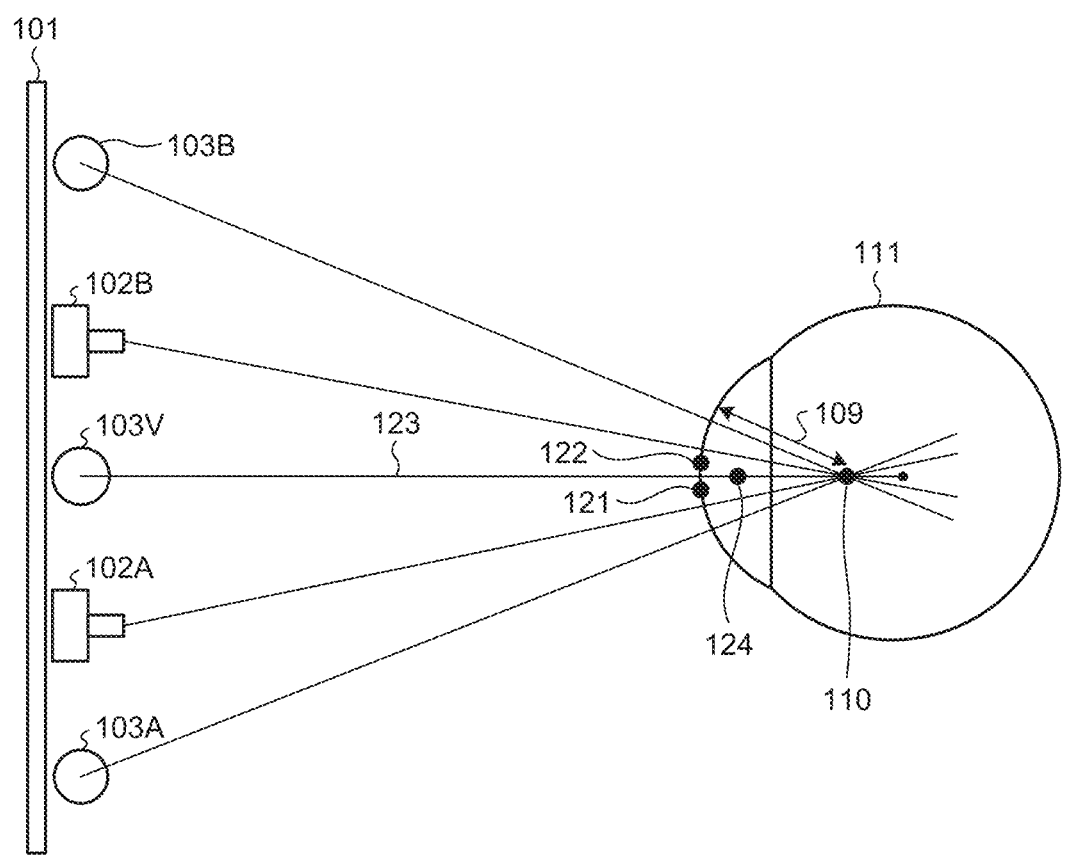
FIG. 6 is another schematic diagram for illustrating the method for calculating the positional data of the corneal curvature center according to the first embodiment.

FIGS. 5 and 6 are schematic diagrams for illustrating a method for calculating the positional data of the corneal curvature center 110 according to the present embodiment. FIG. 5 illustrates an exemplary case where the eyeball 111 is illuminated by one light source 103C. FIG. 6 illustrates an exemplary case where the eyeball 111 is illuminated by the first light source 103A and the second light source 103B.

First, the exemplary case illustrated in FIG. 5 will be described. The light source 103C is disposed between the first camera 102A and the second camera 102B. A pupil center 112C is a center of the pupil 112. A corneal reflection center 113C is a center of the corneal reflection image 113. In FIG. 5, the pupil center 112C indicates the pupil center at the time when the eyeball 111 is illuminated by one light source 103C. The corneal reflection center 113C indicates the corneal reflection center at the time when the eyeball 111 is illuminated by one light source 103C.

The corneal reflection center 113C exists on a straight line connecting the light source 103C and the corneal curvature center 110. The corneal reflection center 113C is positioned at a middle point between the corneal surface and the corneal curvature center 110. A corneal curvature radius 109 is a distance between the corneal surface and the corneal curvature center 110.

Positional data of the corneal reflection center 113C is detected by the stereo camera device 102. The corneal curvature center 110 exists on a straight line connecting the light source 103C and the corneal reflection center 113C. The curvature center calculation unit 214 calculates positional data at which a distance from the corneal reflection center 113C on the straight line corresponds to a predetermined value as positional data of the corneal curvature center 110. The predetermined value is a value determined in advance from a general curvature radius value of the cornea, which is stored in the storage 220.

Next, the exemplary case illustrated in FIG. 6 will be described. In the present embodiment, the first camera 102A and the second light source 103B, and the second camera 102B and the first light source 103A are symmetrically disposed with respect to a straight line passing through an intermediate position between the first camera 102A and the second camera 102B. It can be assumed that a virtual light source 103V exists at the intermediate position between the first camera 102A and the second camera 102B.

A corneal reflection center 121 indicates a corneal reflection center in the image of the eyeball 111 captured by the second camera 102B. A corneal reflection center 122 indicates a corneal reflection center in the image of the eyeball 111 captured by the first camera 102A. A corneal reflection center 124 indicates a corneal reflection center corresponding to the virtual light source 103V.

Positional data of the corneal reflection center 124 is calculated based on positional data of the corneal reflection center 121 and positional data of the corneal reflection center 122 obtained by the stereo camera device 102. The stereo camera device 102 detects the positional data of the corneal reflection center 121 and the positional data of the corneal reflection center 122 in a local coordinate system defined by the stereo camera device 102. Camera calibration based on a stereo calibration method is performed on the stereo camera device 102 in advance, and a conversion parameter for converting the three-dimensional local coordinate system of the stereo camera device 102 into a three-dimensional global coordinate system is calculated. The conversion parameter is stored in the storage 220.

The curvature center calculation unit 214 converts, using the conversion parameter, the positional data of the corneal reflection center 121 and the positional data of the corneal reflection center 122 obtained by the stereo camera device 102 into positional data in the global coordinate system. The curvature center calculation unit 214 calculates the positional data of the corneal reflection center 124 in the global coordinate system based on the positional data of the corneal reflection center 121 and the positional data of the corneal reflection center 122 defined in the global coordinate system.

The corneal curvature center 110 exists on a straight line 123 connecting the virtual light source 103V and the corneal reflection center 124. The curvature center calculation unit 214 calculates positional data at which a distance from the corneal reflection center 124 on the straight line 123 corresponds to a predetermined value as positional data of the corneal curvature center 110. The predetermined value is a value determined in advance from a general curvature radius value of the cornea, which is stored in the storage 220.

As described with reference to FIG. 6, even in a case where there are two light sources, the corneal curvature center 110 is calculated according to the method similar to the method of a case where there is one light source.

A corneal curvature radius 109 is a distance between the corneal surface and the corneal curvature center 110. Therefore, the corneal curvature radius 109 is calculated by calculating the positional data of the corneal surface and the positional data of the corneal curvature center 110.

In this manner, in the present embodiment, the positional data of the corneal curvature center 110, the positional data of the corneal reflection center 124, and the positional data of the pupil center 112C in the global coordinate system are calculated.

The line-of-sight detection unit 216 is capable of detecting the line-of-sight vector of the subject based on the positional data of the pupil center 112C and the positional data of the corneal curvature center 110. Further, the distance data acquisition unit 218 is capable of obtaining the distance data between the display screen of the display device 101 and the face of the subject including the eyeball 111 based on the positional data of the pupil center 112C.

[Method for Detecting Line of Sight]

Next, an example of a method for detecting a line of sight according to the present embodiment will be described. FIG. 7 is a flowchart illustrating an example of a method for detecting a line of sight according to the present embodiment. In the present embodiment, a positioning support process for adjusting the line-of-sight detection device 100 and the subject to a proper relative position (step S100), a calibration process including processing for calculating the positional data of the corneal curvature center 110 and processing for calculating the distance data between the pupil center 112C and the corneal curvature center 110 (step S200), and a line-of-sight detection process (step S300) are performed.

(Positioning Support Process)

The positioning support process will be described. In a case where eyeglasses are worn on the face of the subject, there is a possibility that at least a part of the detection light emitted from the light source 103 onto the face of the subject is reflected by the lens of the eyeglasses.

Figure 9:
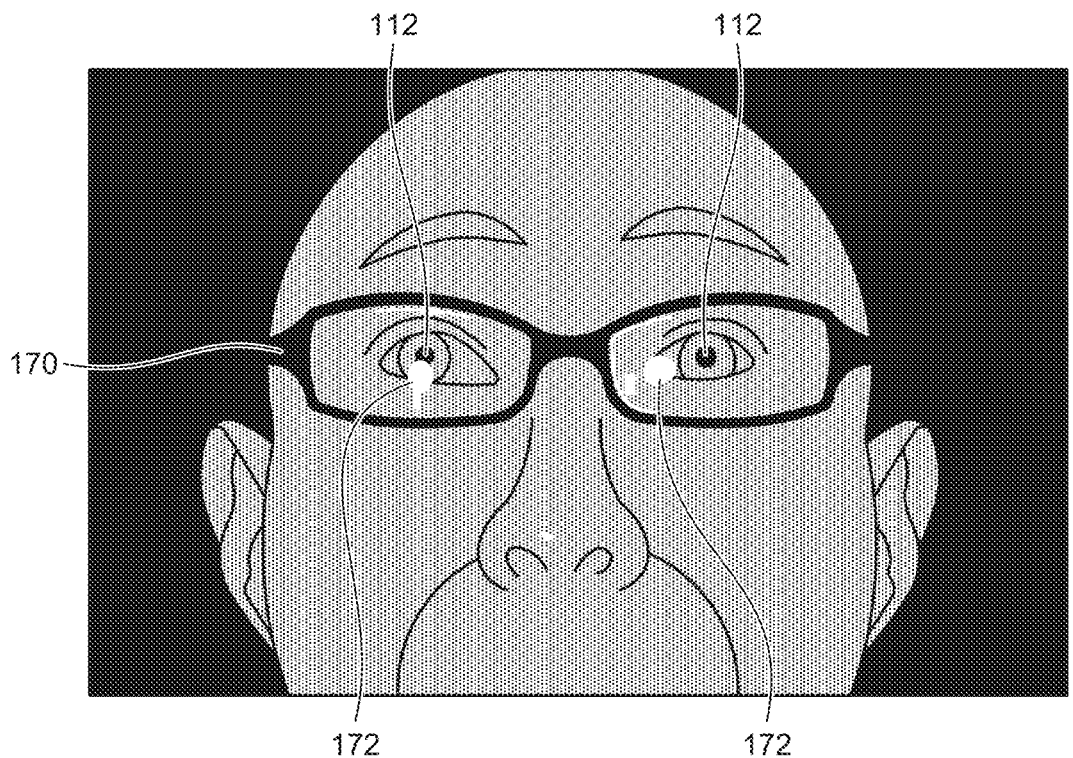
FIG. 9 is a schematic view illustrating a state in which at least a part of a reflection image of the light source on the eyeglasses overlaps the pupil of the subject in a visual field area of the stereo camera device.

FIG. 8 is a diagram schematically illustrating a relationship among the pupil 112 of the subject wearing eyeglasses 170, the stereo camera device 102, and the light source 103. FIG. 8 illustrates a state in which a position of a reflection image 172 of the light source 103 on the eyeglasses 170 and the position of the pupil 112 of the subject coincide with each other in the visual field area of the stereo camera device 102. FIG. 9 is a schematic view illustrating a state in which at least a part of the reflection image 172 of the light source 103 on the eyeglasses 170 overlaps the pupil 112 of the subject in the visual field area of the stereo camera device 102.

As illustrated in FIGS. 8 and 9, the reflection image 172 of the light source 103 is formed on the lens of the eyeglasses 170, and in a case where the reflection image 172 and the pupil 112 of the subject overlap in the visual field area of the stereo camera device 102, it is difficult for the stereo camera device 102 to obtain image data of the pupil 112 of the subject and the corneal reflection image 113 excellently. When the pupil 112 and the corneal reflection image 113 are not detected excellently, the detection accuracy of the line of sight of the subject is lowered.

Figure 10:
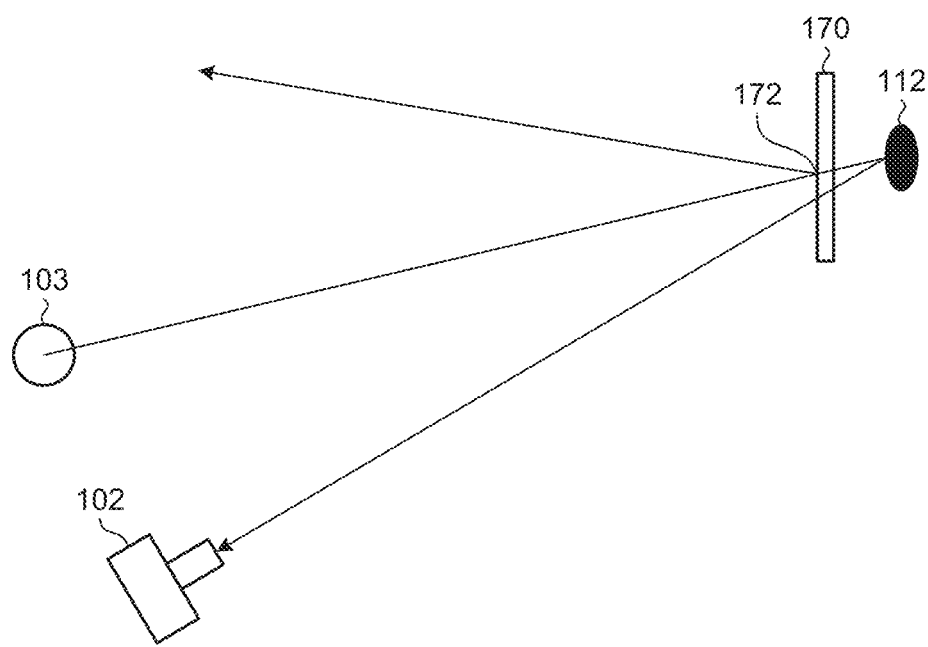
FIG. 10 is a diagram schematically illustrating the relationship among the pupil of the subject wearing the eyeglasses, the stereo camera device, and the light source.

FIG. 10 is a schematic diagram illustrating a state in which the position of the reflection image 172 of the light source 103 on the eyeglasses 170 and the position of the pupil 112 of the subject do not coincide with each other in the visual field area of the stereo camera device 102. As illustrated in FIG. 10, in a case where the reflection image 172 of the light source 103 is formed on the lens of the eyeglasses 170 but does not overlaps the pupil 112 of the subject in the visual field area of the stereo camera device 102, the stereo camera device 102 can obtain the image data of the pupil 112 of the subject and the corneal reflection image 113 excellently. When the pupil 112 and the corneal reflection image 113 are detected excellently, a decrease in detection accuracy of the line of sight of the subject is suppressed.

In the present embodiment, before the calibration process (step S200) and the line-of-sight detection process (step S300) are started, the line-of-sight detection device 100 supports the subject or a measurer such that the relative positions of the subject wearing the eyeglasses 170, the stereo camera device 102, and the light source 103 enter a state illustrated in FIG. 10. That is, before the calibration process (step S200) and the line-of-sight detection process (step S300) are started, the line-of-sight detection device 100 executes processing for prompting the subject or the measurer to adjust at least one of the position of the face of the subject, the orientation of the face, the position of the eyeglasses 170, and the orientation of the eyeglasses 170 so that the reflection image 172 and the eye of the subject do not overlap in the visual field area of the stereo camera device 102.

Figure 11:
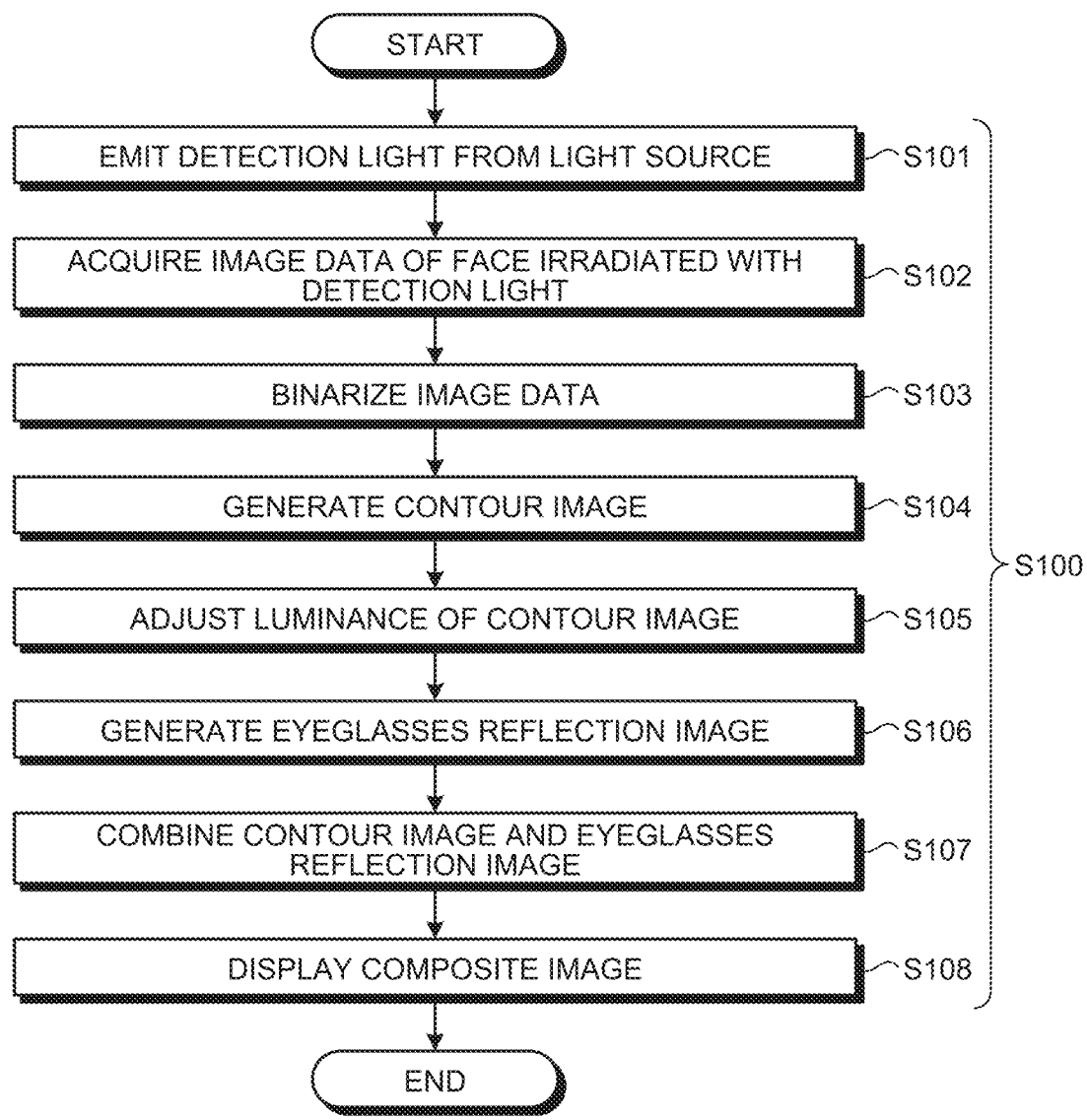
FIG. 11 is a flowchart illustrating an exemplary positioning support process according to the first embodiment.

FIG. 11 is a flowchart illustrating an exemplary positioning support process according to the present embodiment. As illustrated in FIG. 11, the positioning support process (step S100) includes a step for emitting the detection light from the light source 103 onto the face of the subject (step S101), a step for acquiring image data of the face of the subject irradiated with the detection light emitted from the light source 103 (step S102), a step for binarizing the obtained image data (step S103), a step for generating a feature image indicating an image of a feature portion within the face from the binarized image data (step S104), a step for adjusting luminance of the generated feature image (step S105), a step for generating an eyeglasses reflection image indicating the reflection image 172 of the light source 103 on the eyeglasses 170 worn on the face of the subject (step S106), a step for combining the feature image and the eyeglasses reflection image (step S107), and a step for causing the display device 101 to display a composite image in which the feature image and the eyeglasses reflection image are combined (step S108).

The light source 103 emits the detection light (step S101). The stereo camera device 102 obtains image data of the face of the subject onto which the detection light is emitted. At least one of the first camera 102A and the second camera 102B obtains the image data of the face of the subject. In the present embodiment, the first camera 102A obtains the image data of the face of the subject. Note that the second camera 102B may obtain the image data of the face of the subject. Note that both the image data obtained by the first camera 102A and the image data obtained by the second camera 102B may be used.

Figure 12:
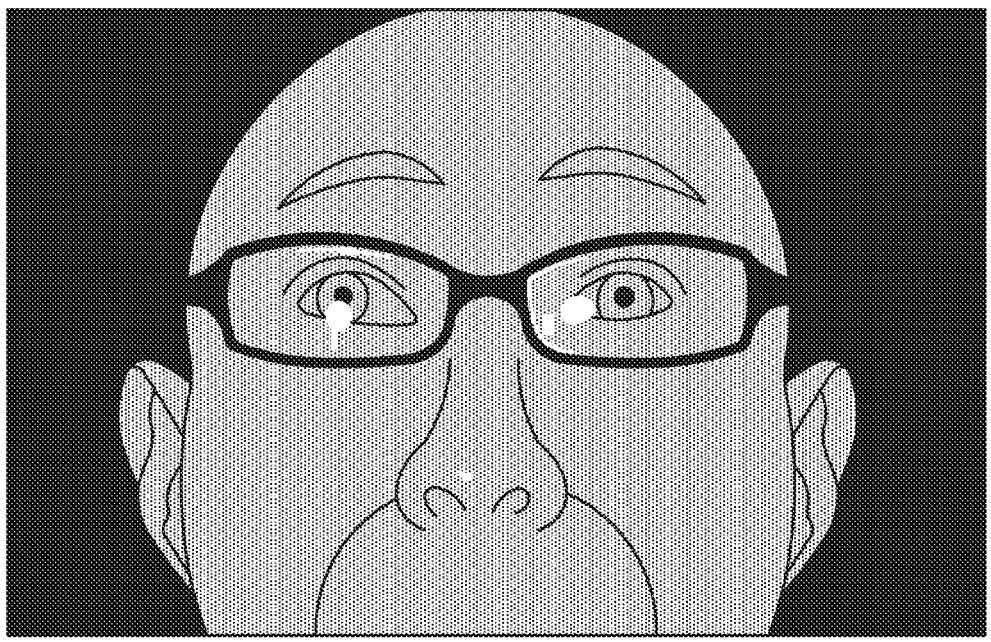
FIG. 12 is a view schematically illustrating exemplary image data obtained by an image data acquisition unit according to the first embodiment.

The image data acquisition unit 202 acquires the image data of the face of the subject onto which the detection light is emitted from the stereo camera device 102 (step S102). FIG. 12 is a view schematically illustrating exemplary image data acquired by the image data acquisition unit 202 according to the present embodiment. FIG. 12 illustrates raw data that is image data before being subject to image processing, which is obtained by the stereo camera device 102 at the time when the infrared light as the detection light is emitted onto the face of the subject.

Figure 13:
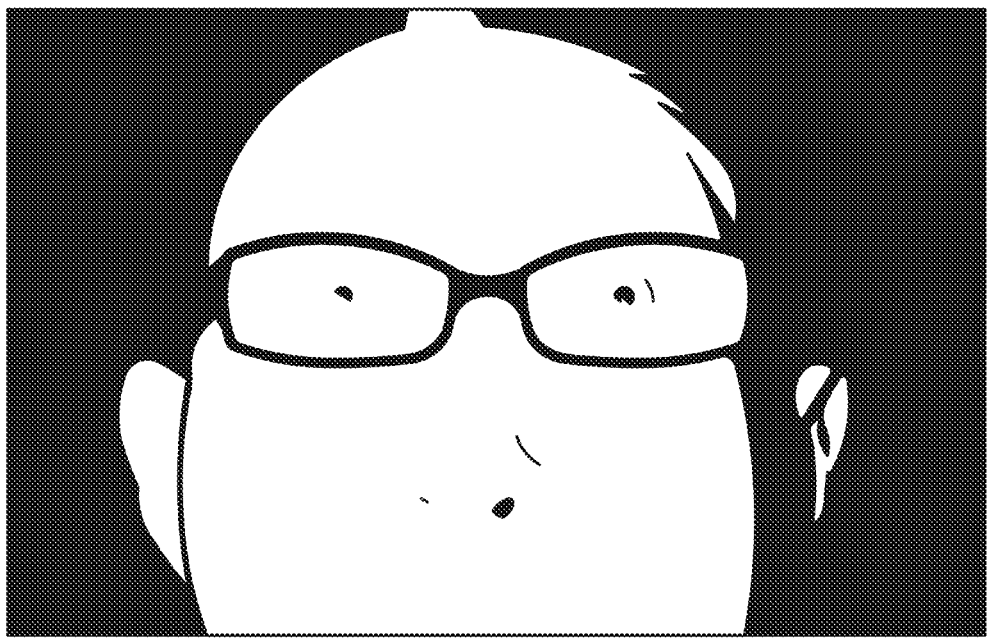
FIG. 13 is a view schematically illustrating exemplary binarized image data according to the first embodiment.

The image processing unit 206 performs image processing on the image data acquired by the image data acquisition unit 202. In the present embodiment, the image processing unit 206 binarizes the image data acquired by the image data acquisition unit 202 (step S103). FIG. 13 is a view schematically illustrating exemplary binarized image data according to the present embodiment.

The binarization of the image data indicates processing for converting the image data including a plurality of pixels into two tones of black and white based on a predetermined threshold value. In step S103, the binarization is performed based on a predetermined first threshold value. When luminance of the pixel is equal to or higher than the first threshold value, the image processing unit 206 replaces the pixel with white color, and replaces the pixel with black color when the luminance of the pixel is lower than the first threshold value. Note that the first threshold value in the binarization may be a fixed value set in advance, an intermediate value between the highest value and the lowest value among the luminance of the plurality of pixels of the obtained image data, or an intermediate value in luminance distribution. The binarization may be performed based on at least one of the P-tile method in which the first threshold value is determined according to a ratio of white pixels in the binarized result image, the modal method in which the bottom value of a valley of a histogram is set to the first threshold value when the luminance histogram has two maximum values, and the discriminant analysis method in which the first threshold value is determined such that, when the luminance histogram of the image is divided into two classes at a certain threshold value, the interclass variance becomes the largest.

Figure 14:
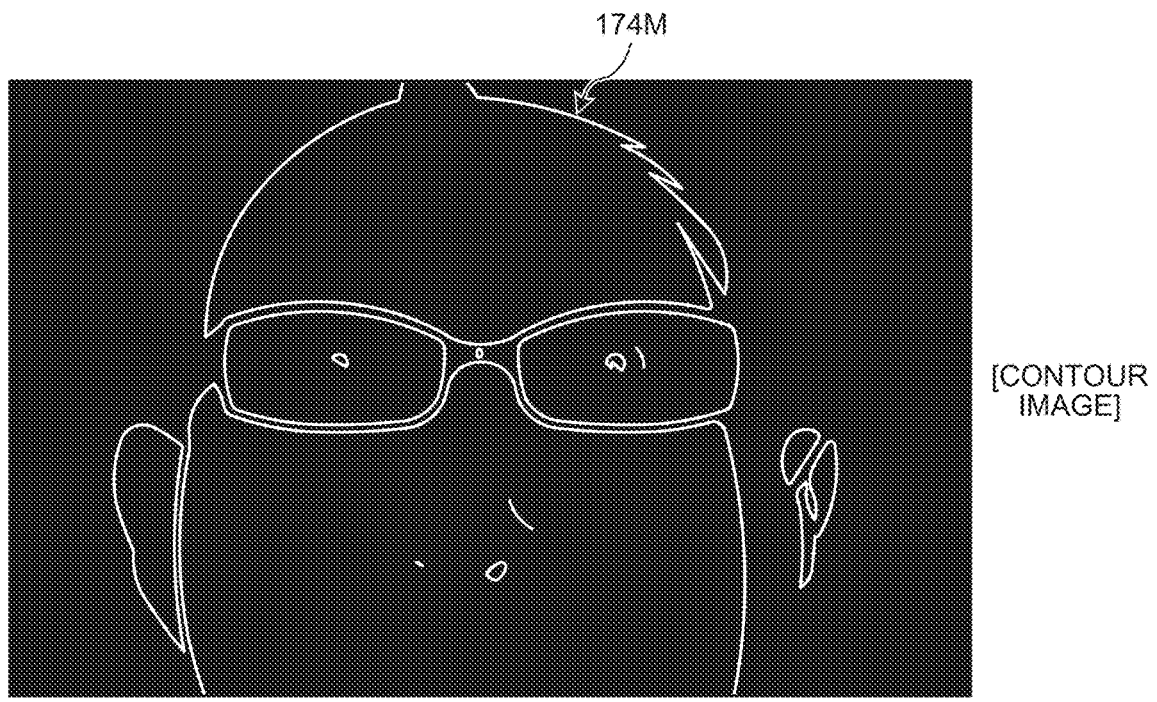
FIG. 14 is a view schematically illustrating an exemplary feature image of the face of the subject according to the first embodiment.

Next, the image processing unit 206 generates, from the binarized image data, the feature image indicating the image of the feature portion within the face (step S104). In the present embodiment, the feature image includes a contour image of the face of the subject. FIG. 14 is a view schematically illustrating an exemplary contour image 174M of the face of the subject according to the present embodiment. As illustrated in FIG. 14, in the present embodiment, the contour image 174M includes an edge image indicating a boundary between a white portion and a black portion of the binarized image data. The luminance of the contour image 174M generated in step S104 is equal to or higher than the first threshold value.

When generating the feature image, the image processing unit 206 performs edge detection on the binarized image data. The edge detection of the image data indicates processing for detecting a boundary where the luminance of a pixel rapidly changes in the image data including a plurality of pixels. For example, the image processing unit 206 may carry out differential processing on the luminance of adjacent pixels to perform the edge detection, or may carry out template matching to perform the edge detection. The edge detection of the image data is performed, thereby generating the contour image 174M of the face of the subject as illustrated in FIG. 14.

The contour image 174M of the face includes at least one of a contour image of the face of the subject, a contour image of the eyelid of the subject, a contour image of the pupil of the subject, a contour image of the naris of the subject, a contour image of the mouth of the subject, and a contour image of the eyeglasses 170 worn on the face of the subject. In the present embodiment, the contour image 174M is required to be an image that allows the subject or the measurer to recognize or estimate, when viewing the contour image 174M, the position of the pupil 112 from the contour image 174M.

Figure 15:
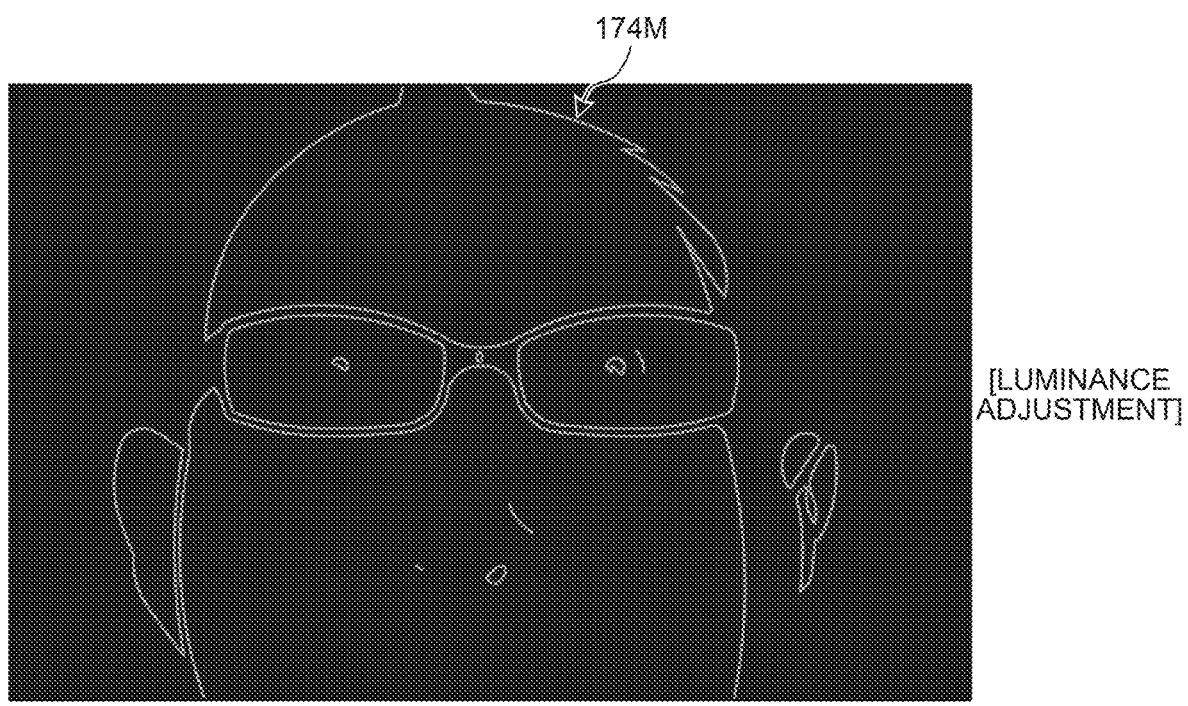
FIG. 15 is a view schematically illustrating an exemplary feature image with reduced luminance according to the first embodiment.

Next, the image processing unit 206 adjusts the luminance of the generated contour image 174M (step S105). In the present embodiment, the image processing unit 206 reduces the luminance of the contour image 174M generated in step S104. The luminance of the contour image 174M generated in step S105 is lower than the first threshold value. FIG. 15 is a view schematically illustrating an example of the contour image 174M with the reduced luminance according to the present embodiment. FIG. 15 illustrates an exemplary case where the luminance of the contour image 174M is reduced to 50%.

Figure 16:
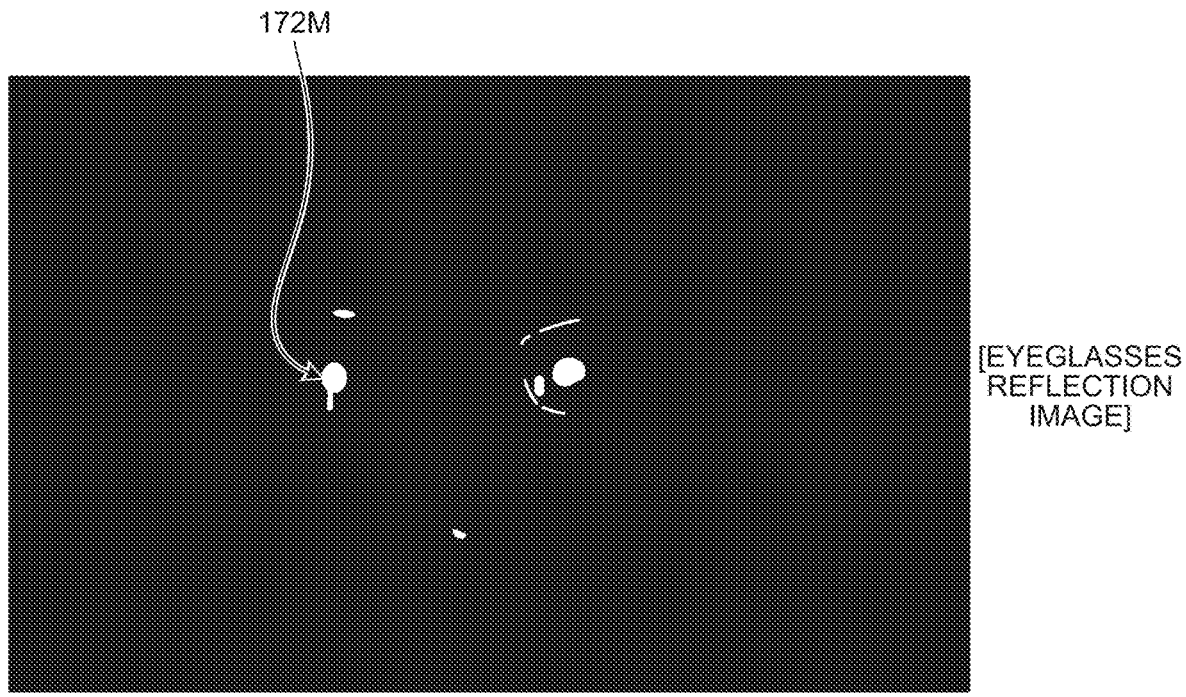
FIG. 16 is a view schematically illustrating an exemplary eyeglasses reflection image according to the first embodiment.

Further, the image processing unit 206 generates the eyeglasses reflection image indicating the reflection image 172 of the light source 103 on the eyeglasses 170 worn on the face of the subject (step S106). FIG. 16 is a view schematically illustrating an example of the eyeglasses reflection image 172M according to the present embodiment. In the present embodiment, the image processing unit 206 binarizes the image data obtained in step S102 (see FIG. 12) to generate the eyeglasses reflection image 172M.

In step S106, a second threshold value, which is higher than the first threshold value predetermined in step S103, is predetermined. The image processing unit 206 binarizes the image data obtained by the image data acquisition unit 202 based on the second threshold value higher than the first threshold value. When the luminance of the pixel is equal to or higher than the second threshold value, the image processing unit 206 replaces the pixel with white color, and replaces the pixel with black color when the luminance of the pixel is lower than the second threshold value. As a result, only the reflection image 172 with high luminance is extracted, and the eyeglasses reflection image 172M as illustrated in FIG. 16 is generated.

Figure 17:
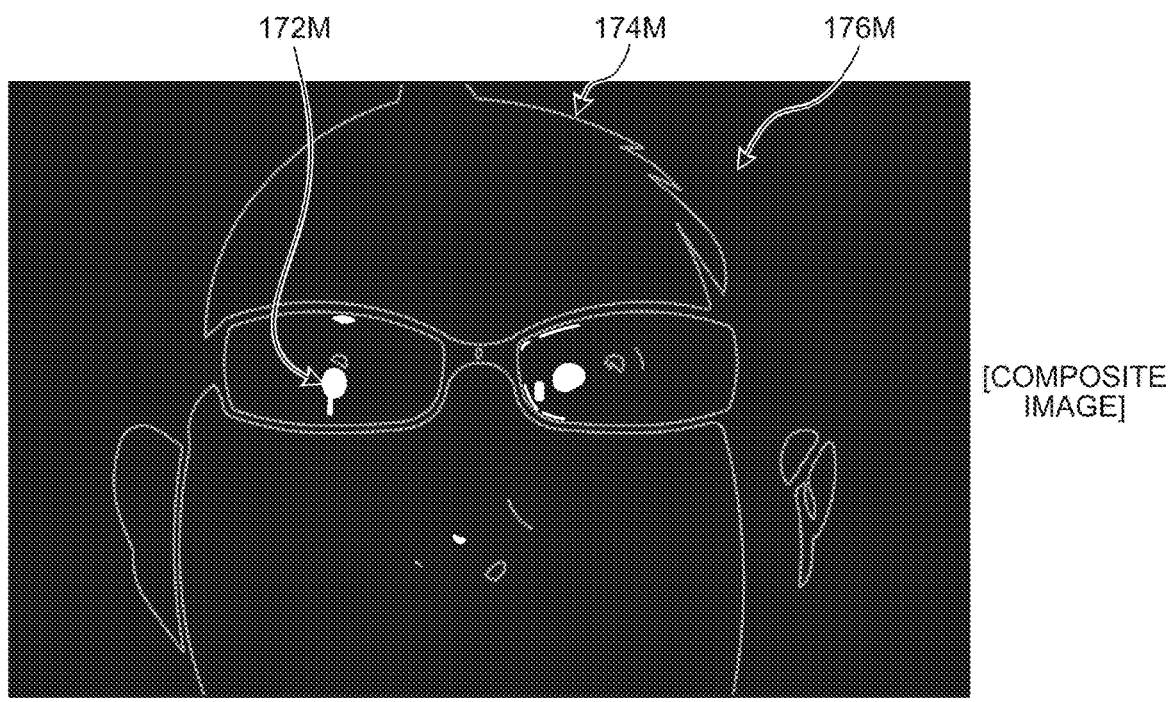
FIG. 17 is a view schematically illustrating an exemplary composite image obtained by combining the feature image and the eyeglasses reflection image according to the first embodiment.

Next, the image processing unit 206 combines the contour image 174M generated in step S104 and the luminance thereof is adjusted in step S105 (see FIG. 15) and the eyeglasses reflection image 172M generated in step S106 (see FIG. 16) to generate a composite image 176M (step S107). FIG. 17 is a view schematically illustrating an example of the composite image 176M obtained by combining the contour image 174M and the eyeglasses reflection image 172M according to the present embodiment. As illustrated in FIG. 17, in the composite image 176M, the luminance of the eyeglasses reflection image 172M is higher than the luminance of the contour image 174M.

The contour image 174M includes pixels indicating a contour and pixels indicating a background other than the contour. The eyeglasses reflection image 172M includes pixels indicating the reflection image 172 and pixels indicating a background other than the reflection image 172. In combining the contour image 174M and the eyeglasses reflection image 172M, the pixels of the contour image 174M are combined with the pixels of the eyeglasses reflection image 172M corresponding to the pixels of the contour image 174M. The luminance of the pixels of the contour image 174M is multivalued, and the pixel indicating the contour in the contour image 174M can be assumed to be gray color. The pixel 172M indicating the reflection image 172 in the eyeglasses reflection image can be assumed to be white color. The pixel indicating the background other than the contour in the contour image 174M and the pixel indicating the background other than the reflection image 172 in the eyeglasses reflection image 172M can be assumed to be black color. When any two pixels of a white pixel, a gray pixel, and a black pixel are combined in combining the pixel of the contour image 174M and the pixel of the eyeglasses reflection image 172M corresponding to the pixel of the contour image 174M, a pixel having high luminance is selected as a pixel of the composite image 176M. That is, when a gray pixel included in the contour image 174M indicating the contour is combined with a black pixel included in the eyeglasses reflection image 172M indicating the background, a pixel of the composite image 176M in which the contour image 174M and the eyeglasses reflection image 172M are combined is gray. When a black pixel included in the contour image 174M indicating the background is combined with a white pixel included in the eyeglasses reflection image 172M indicating the reflection image 172, a pixel of the composite image 176M in which the contour image 174M and the eyeglasses reflection image 172M are combined is white.

The display controller 208 causes the display device 101 to display the composite image 176M in which the contour image 174M and the eyeglasses reflection image 172M are combined (step S108). The luminance of the eyeglasses reflection image 172M is higher than that of the contour image 174M. The luminance of the eyeglasses reflection image 172M is equal to or higher than the second threshold value, and the luminance of the contour image 174M is lower than the first threshold value. In the present embodiment, the luminance of the eyeglasses reflection image 172M is 100%, and the luminance of the contour image 174M is 50%. Therefore, the eyeglasses reflection image 172M is displayed on the display device 101 in an emphasized manner compared with the contour image 174M.

Figure 18:
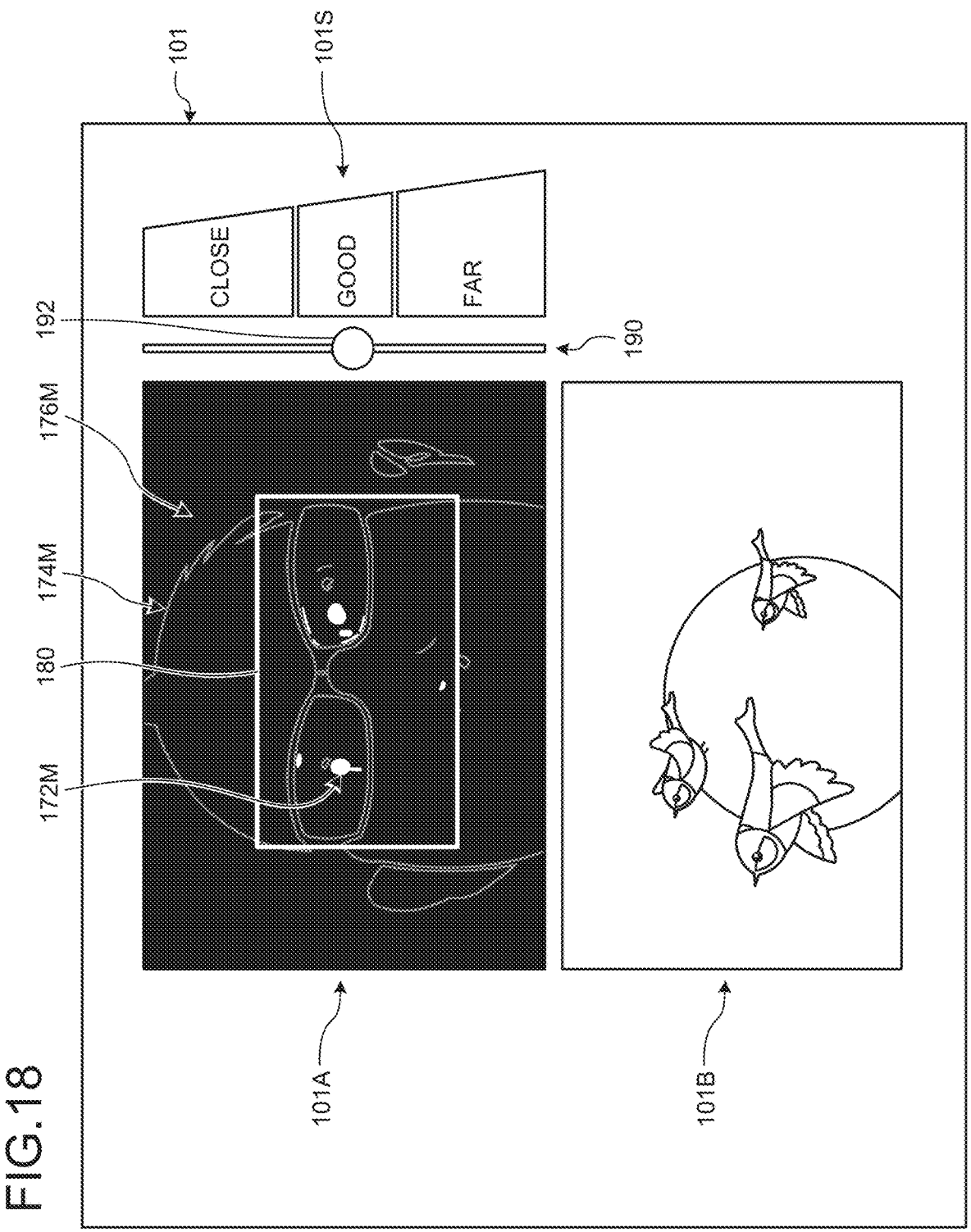
FIG. 18 is a view illustrating an example of the display device according to the first embodiment.

FIG. 18 is a view illustrating an example of the display device 101 according to the present embodiment. As illustrated in FIG. 18, the display controller 208 forms, on the display screen 101S of the display device 101, a first display area 101A for displaying the composite image 176M in which the eyeglasses reflection image 172M and the contour image 174M are combined, and a second display area 101B for displaying animations. As illustrated in FIG. 18, the display controller 208 causes the display device 101 to display the eyeglasses reflection image 172M with the luminance higher than that of the contour image 174M.

In the present embodiment, the display controller 208 causes the display device 101 to display the eyeglasses reflection image 172M with the luminance equal to or higher than the second threshold value, and causes the display device 101 to display the contour image 174M with the luminance lower than the first threshold value.

Further, in the present embodiment, the display controller 208 causes the display device 101 to display the contour image 174M and the eyeglasses reflection image 172M in different colors. In the present embodiment, the display controller 208 displays the contour image 174M in orange color, and displays the eyeglasses reflection image 172M in yellow color. Note that the display controller 208 may cause the display device 101 to display the contour image 174M and the eyeglasses reflection image 172M with different lightness or different saturation. For example, the eyeglasses reflection image 172M may be displayed on the display device 101 with lightness or saturation higher than that of the contour image 174M.

The computer system 20 performs real-time image processing on the image data of the face of the subject obtained by the stereo camera device 102, and displays it in the first display area 101A of the display device 101. That is, a moving image of the composite image 176M is displayed on the display device 101.

As the composite image 176M is displayed on the display device 101, the subject or the measurer can adjust the position or the orientation of the face of the subject or can adjust the position or the orientation of the eyeglasses 170 such that the reflection image 172 of the light source 103 and the eye of the subject do not overlap in the visual field area of the stereo camera device 102 while viewing the composite image 176M displayed on the display device 101. In this manner, since the image of the subject having been subject to the image processing is displayed on the display device 101, the subject or the measurer can adjust the position or the orientation of the face of the subject or can adjust the position or the orientation of the eyeglasses 170 without a sense of discomfort or aversion.

Further, in the present embodiment, the display controller 208 causes the display screen 101S of the display device 101 to display a guide line 180 with a fixed dimension and position on the display screen 101S. In the present embodiment, the guide line 180 forms a rectangular shape. The guide line 180 is displayed to overlap the composite image 176M in the first display area 101A. The subject or the measurer can adjust the position of the face of the subject such that the eyes of the subject are placed inside the rectangular guide line 180 while viewing the composite image 176M.

In the second display area 101B, animations are displayed at an infant medical examination, for example. In the infant medical examination, detection of a line of sight of an infant is performed in a state where the infant is sitting on parent's knees sitting on a chair. The relative position between the line-of-sight detection device 100 and the face of the infant is adjusted by the parent adjusting the position or the orientation of the face of the infant or by the measurer adjusting the position or the orientation of the line-of-sight detection device 100. While the relative position between the line-of-sight detection device 100 and the face of the infant is adjusted, animations for attracting the infant's attention are displayed in the second display area 101B to make the infant gaze at the display device 101. The display data displayed in the second display area 102B may be a moving image or a still image. Any display data that can attract the infant's attention may be used.

Further, in the present embodiment, the distance data acquisition unit 218 obtains distance data between the display screen 101S of the display device 101 and the eye or the face of the subject. The distance data acquisition unit 218 detects the pupil 112 based on the image data of the eyeball 111 of the subject obtained by the stereo camera device 102, and calculates the position of the pupil center 112C in the global coordinate system. By calculating the position of the pupil center 112C in the global coordinate system, the distance data acquisition unit 218 can calculate the distance between the center of the display screen 101S of the display device 101 and the eye of the subject.

The display controller 208 causes the display device 101 to display the distance data obtained by the distance data acquisition unit 218.

In the present embodiment, image data of a scale 190 indicating the distance between the display screen 101S of the display device 101 and the eye of the subject is displayed on the display device 101. In addition, as a guide of the distance between the display screen 101S of the display device 101 and the eye of the subject, character data of "close", "good", and "far" are displayed on the display device 101. The display controller 208 moves an indicator 192 along the scale 190 based on the distance data obtained by the distance data acquisition unit 218. When the distance between the display screen 101S of the display device 101 and the eye of the subject is a proper value, the display controller 208 moves the indicator 192 to "good". When the distance between the display screen 101S of the display device 101 and the eye of the subject is shorter than the proper value, the display controller 208 moves the indicator 192 to "close". When the distance between the display screen 101S of the display device 101 and the eye of the subject is longer than the proper value, the display controller 208 moves the indicator 192 to "far".

The face of the subject is preferably located at a focal position of the optical system of the stereo camera device 102. The proper value of the distance between the display screen 101S of the display device 101 and the eye of the subject is a distance at which the eye or the face of the subject is located at the focal position of the optical system of the stereo camera device 102. The subject or the measurer can adjust the position of the face of the subject such that the indicator 192 is placed at the position of "good" while viewing the indicator 192.

In this manner, the positioning support process is performed.

(Calibration Process)

Next, the calibration process will be described. In the present embodiment, after the positioning support process (step S100) is performed, the calibration process, which includes the processing for calculating the positional data of the corneal curvature center 110 and the processing for calculating the distance data between the pupil center 112C and the corneal curvature center 110, is performed (step S200).

Figure 19:
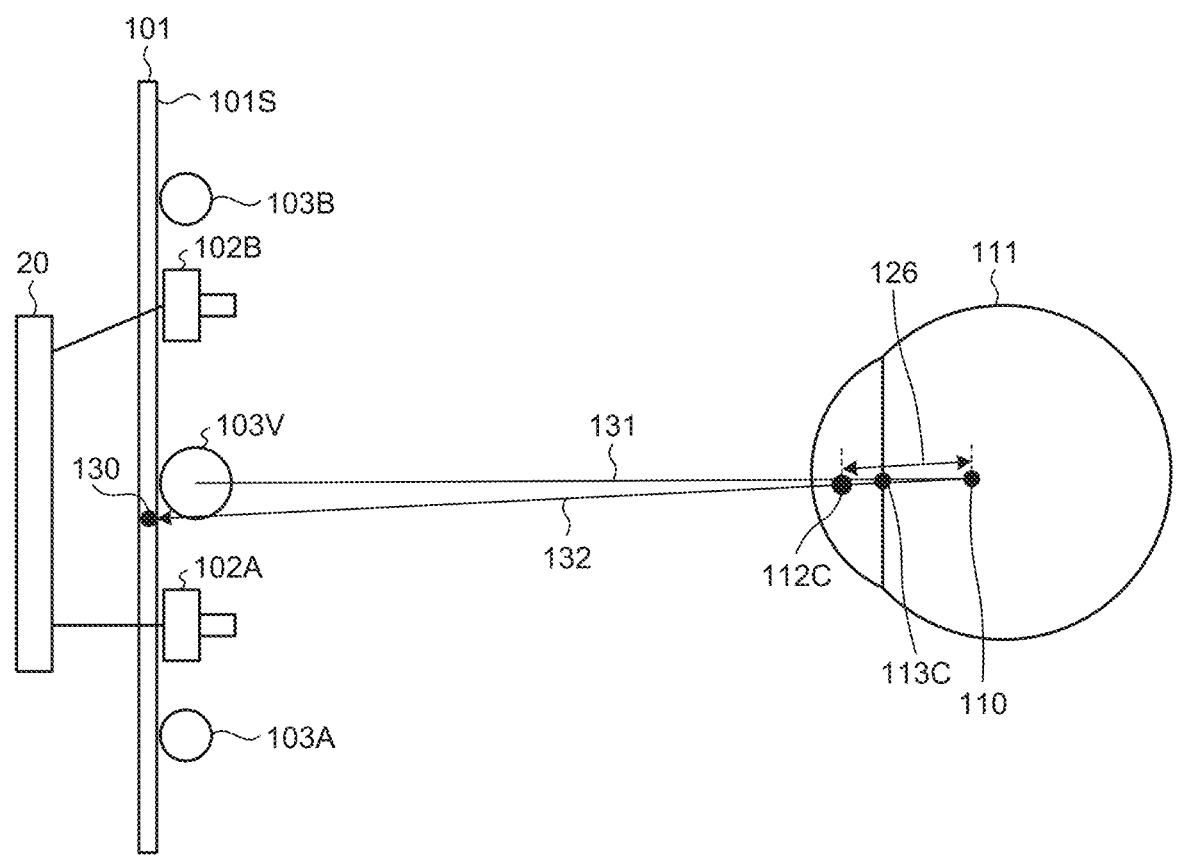
FIG. 19 is a schematic diagram for illustrating exemplary calibration processing according to the first embodiment.

FIG. 19 is a schematic diagram for illustrating an example of the calibration processing according to the present embodiment. The calibration processing includes calculation of the positional data of the corneal curvature center 110, and calculation of a distance 126 between the pupil center 112C and the corneal curvature center 110.

A target position 130 for making the subject gaze is set. The target position 130 is defined in the global coordinate system. In the present embodiment, the target position 130 is set at a central position of the display screen 101S of the display device 101, for example. Note that the target position 130 may be set at the end position of the display screen 101S.

The display controller 208 displays a target image at the set target position 130. Accordingly, the subject can easily gaze at the target position 130.

A straight line 131 is a straight line connecting the virtual light source 103V and the corneal reflection center 113C. A straight line 132 is a straight line connecting the target position 130 and the pupil center 112C. The corneal curvature center 110 is an intersection point of the straight line 131 and the straight line 132. The curvature center calculation unit 214 can calculate the positional data of the corneal curvature center 110 based on the positional data of the virtual light source 103V, the positional data of the target position 130, the positional data of the pupil center 112C, and the positional data of the corneal reflection center 113C.

Figure 20:
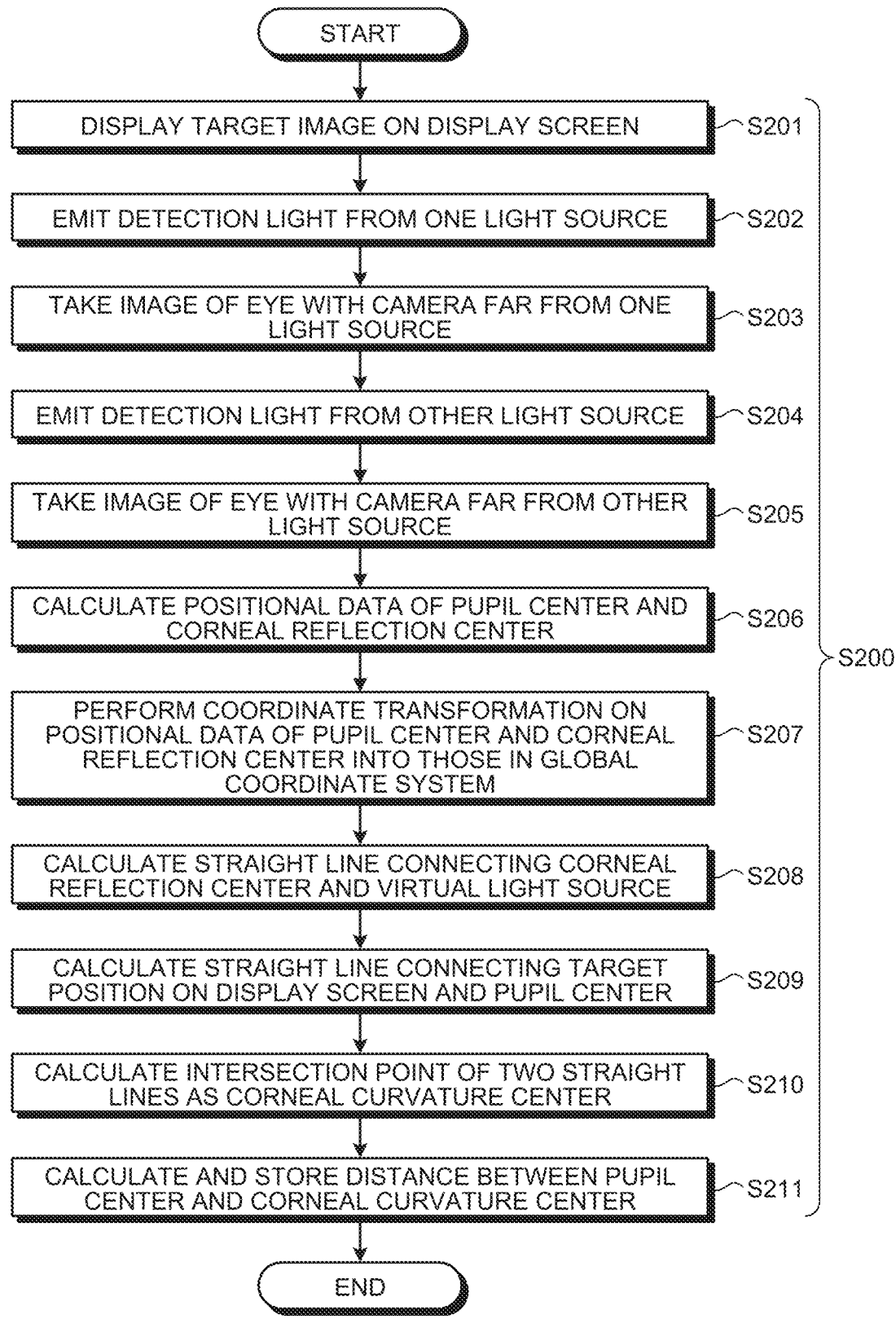
FIG. 20 is a flowchart illustrating the exemplary calibration process according to the first embodiment.

FIG. 20 is a flowchart illustrating an exemplary calibration process (step S200) according to the present embodiment. The output controller 222 causes the display screen 101S of the display device 101 to display the target image (step S201). The subject can gaze at the target position 130 by gazing at the target image.

Next, the light source controller 210 controls the light source drive unit 406 to emit the detection light from one of the first light source 103A and the second light source 103B (step S202). The stereo camera device 102 takes an image of the eye of the subject with the camera having a longer distance from the light source that has emitted the detection light among the first camera 102A and the second camera 102B (step S203).

Next, the light source controller 210 controls the light source drive unit 406 to emit the detection light from the other one of the first light source 103A and the second light source 103B (step S204). The stereo camera device 102 takes an image of the eye of the subject with the camera having a longer distance from the light source that has emitted the detection light among the first camera 102A and the second camera 102B (step S205).

The stereo camera device 102 detects the pupil 112 as a dark portion, and the stereo camera device 102 detects the corneal reflection image 113 as a bright portion. That is, the image of the pupil 112 obtained by the stereo camera device 102 has low luminance, and the image of the corneal reflection image 113 has high luminance. The position detection unit 212 can detect the positional data of the pupil 112 and the positional data of the corneal reflection image 113 based on the luminance of the obtained images. Further, the position detection unit 212 calculates the positional data of the pupil center 112C based on the image data of the pupil 112. Furthermore, the position detection unit 212 calculates the positional data of the corneal reflection center 113C based on the image data of the corneal reflection image 113 (step S206).

The positional data detected by the stereo camera device 102 is positional data defined in the local coordinate system. The position detection unit 212 performs, using a transformation parameter stored in the storage 220, coordinate transformation on the positional data of the pupil center 112C and the positional data of the corneal reflection center 113C detected by the stereo camera device 102, and calculates the positional data of the pupil center 112C and the positional data of the corneal reflection center 113C defined in the global coordinate system (step S207).

The curvature center calculation unit 214 obtains the straight line 131 connecting the corneal reflection center 113C and the virtual light source 103V defined in the global coordinate system (step S208).

Next, the curvature center calculation unit 214 calculates the straight line 132 connecting the target position 130 and the pupil center 112C defined on the display screen 101S of the display device 101 (step S209). The curvature center calculation unit 214 obtains an intersection point of the straight line 131 calculated in step S208 and the straight line 132 calculated in step S209, and sets the intersection point as the corneal curvature center 110 (step S210).

The curvature center calculation unit 214 calculates the distance 126 between the pupil center 112C and the corneal curvature center 110, and stores it in the storage 220 (step S211). The stored distance is used to calculate the corneal curvature center 110 in the line-of-sight detection in step S300.

(Line-of-Sight Detection Process)

Next, the line-of-sight detection process will be described. The line-of-sight detection process is performed after the calibration process. The line-of-sight detection unit 216 calculates the line-of-sight vector and the positional data of the gaze point of the subject based on the image data of the eyeball 111.

Figure 21:
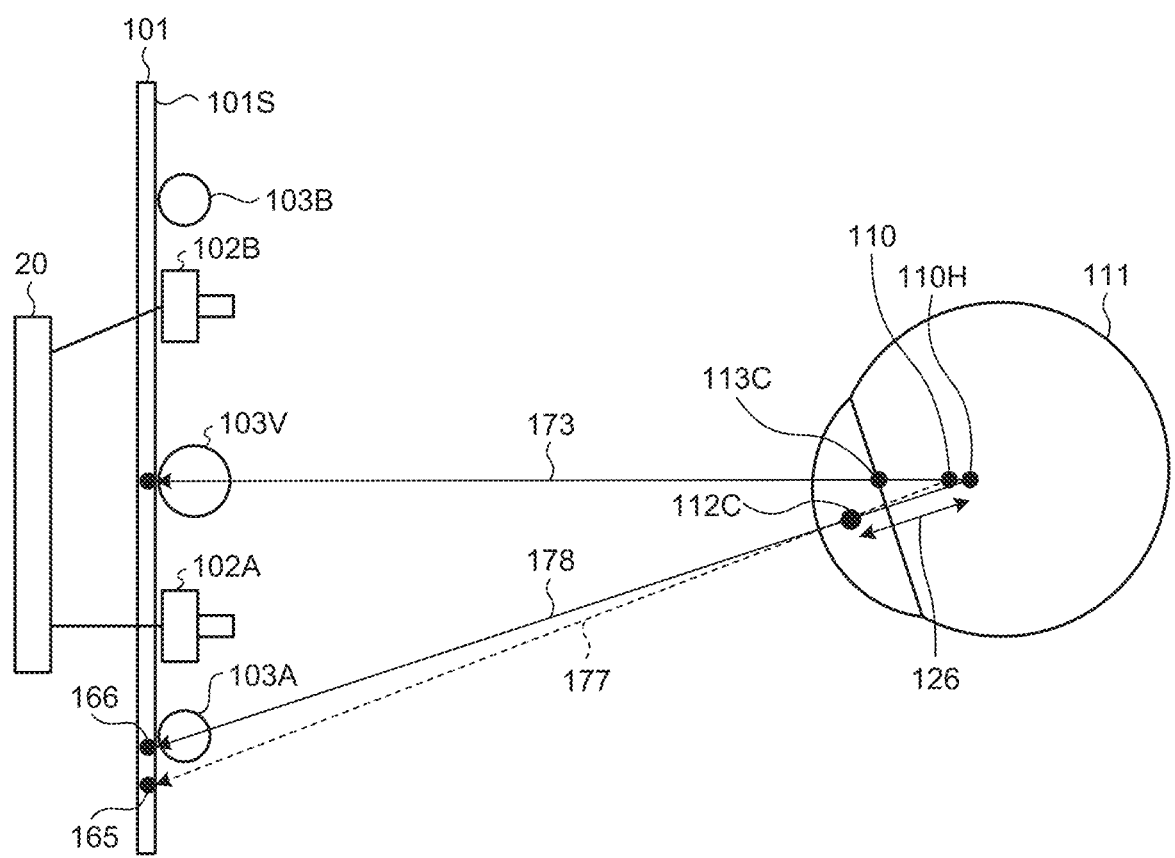
FIG. 21 is a schematic diagram for illustrating exemplary line-of-sight detection processing according to the first embodiment.

FIG. 21 is a schematic diagram for illustrating exemplary line-of-sight detection processing according to the present embodiment. The line-of-sight detection process includes correction of the position of the corneal curvature center 110 using the distance 126 between the pupil center 112C and the corneal curvature center 110 obtained in the calibration process (step S200), and calculation of the gaze point using the positional data of the corrected corneal curvature center 110.

In FIG. 21, a gaze point 165 indicates a gaze point obtained from the corneal curvature center calculated using a general curvature radius value. A gaze point 166 indicates a gaze point obtained from the corneal curvature center calculated using the distance 126 obtained in the calibration process.

The pupil center 112C indicates the pupil center calculated in the calibration process, and the corneal reflection center 113C indicates the corneal reflection center calculated in the calibration process.

A straight line 173 is a straight line connecting the virtual light source 103V and the corneal reflection center 113C. The corneal curvature center 110 is the position of the corneal curvature center calculated from a general curvature radius value.

The distance 126 is a distance between the pupil center 112C calculated in the calibration process and the corneal curvature center 110.

A corneal curvature center 110H indicates a position of the corrected corneal curvature center after the corneal curvature center 110 is corrected using the distance 126.

The corneal curvature center 110H is obtained from the fact that the corneal curvature center 110 exists on the straight line 173 and the distance between the pupil center 112C and the corneal curvature center 110 is the distance 126. As a result, a line of sight 177 calculated in the case where a general curvature radius value is used is corrected to a line of sight 178. Further, the gaze point on the display screen 101S of the display device 101 is corrected from the gaze point 165 to the gaze point 166.

Figure 22:
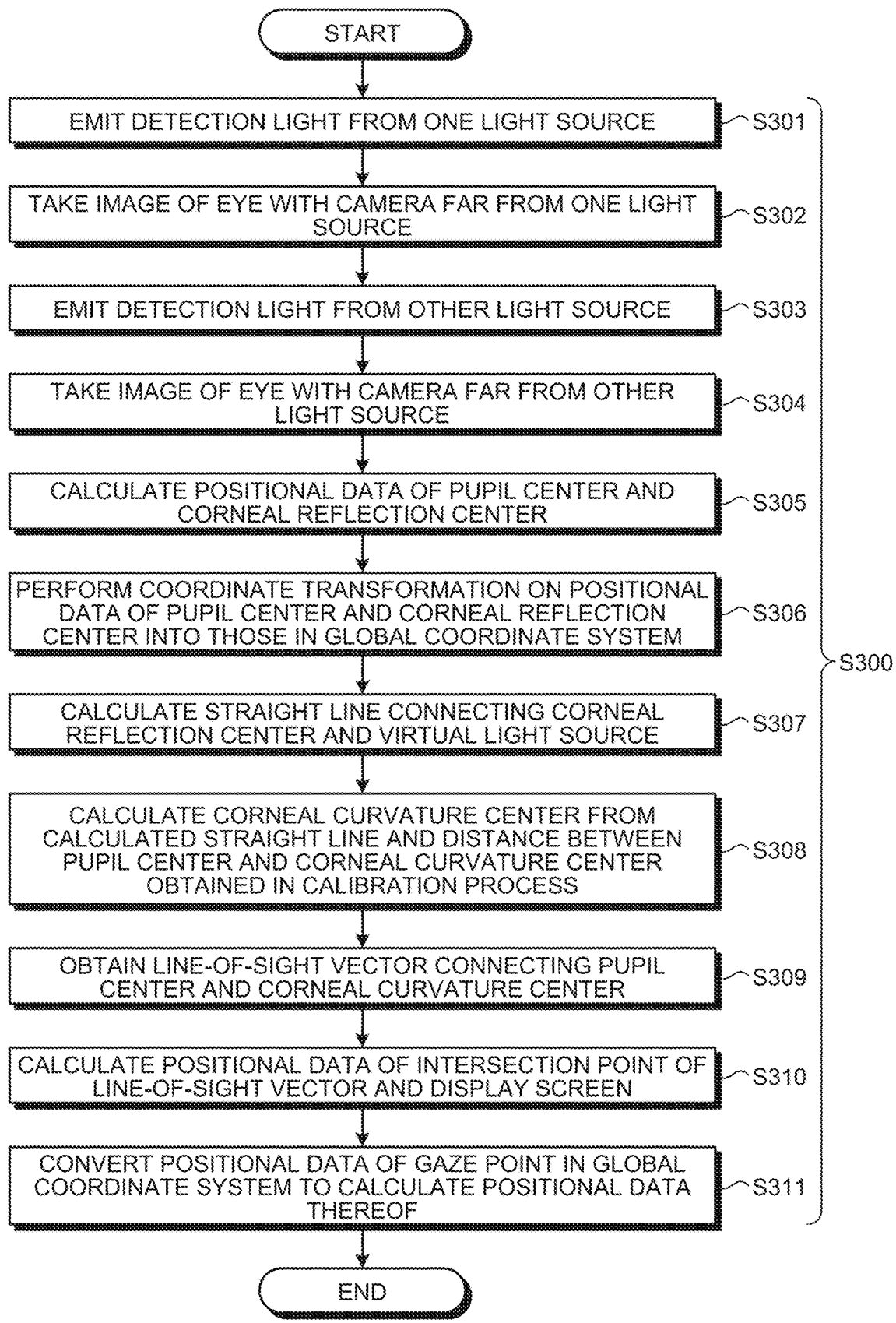
FIG. 22 is a flowchart illustrating the exemplary line-of-sight detection process according to the first embodiment.

FIG. 22 is a flowchart illustrating an exemplary line-of-sight detection process (step S300) according to the present embodiment. Note that the processing from step S301 to step S307 illustrated in FIG. 22 is similar to the processing from step S202 to step S208 illustrated in FIG. 20, and the descriptions thereof will be omitted.

The curvature center calculation unit 214 calculates a position on the straight line 173 calculated in step S307 at which the distance from the pupil center 112C is equal to the distance 126 obtained in the calibration process as the corneal curvature center 110H (step S308).

The line-of-sight detection unit 216 obtains a line-of-sight vector connecting the pupil center 112C and the corneal curvature center 110H (step S309). The line-of-sight vector indicates the line-of-sight direction along which the subject is viewing. The line-of-sight detection unit 216 calculates positional data of the intersection point of the line-of-sight vector and the display screen 101S of the display device 101 (step S310). The positional data of the intersection point of the line-of-sight vector and the display screen 101S of the display device 101 is the positional data of the gaze point of the subject on the display screen 101S defined in the global coordinate system.

The line-of-sight detection unit 216 converts the positional data of the gaze point defined in the global coordinate system into the positional data on the display screen 101S of the display device 101 defined in a two-dimensional coordinate system (step S311). As a result, the positional data of the gaze point on the display screen 101S of the display device 101 viewed by the subject is calculated.

[Action and Effect]

As described above, according to the present embodiment, in the positioning support process (step S100), the image data of the face of the subject obtained by the image data acquisition unit 202 is subject to the image processing in the image processing unit 206. The image processing unit 206 extracts, from the obtained image data, the contour image (feature image) 174M of the face and the eyeglasses reflection image 172M, and generates the composite image 176M. The composite image 176M generated by the image processing unit 206 is displayed on the display device 101. Accordingly, the subject or the measurer can adjust the position or the orientation of the face of the subject or can adjust the position or the orientation of the eyeglasses 170 worn on the face of the subject such that the reflection image 172 of the light source 103 and the eye of the subject do not overlap in the visual field area of the stereo camera device 102 while viewing the composite image 176M displayed on the display device 101. Therefore, in the line-of-sight detection process (step S300) performed after the positioning support process (step S100), the line-of-sight detection is performed in the state where the reflection image 172 of the light source 103 and the eye of the subject do not overlap in the visual field area of the stereo camera device 102. As a result, the pupil 112 and the corneal reflection image 113 are detected excellently with the influence of the reflection image 172 being sufficiently suppressed. Therefore, a decrease in detection accuracy of the line of sight of the subject wearing the eyeglasses 170 is suppressed.

In the present embodiment, the raw data as illustrated in FIG. 12 is not displayed on the display device 101, but the composite image 176M as illustrated in FIGS. 17 and 18 is displayed on the display device 101. In the present embodiment, the detection light emitted onto the subject is infrared light. The raw data of the face of the subject at the time when the infrared light is emitted thereto has a higher possibility of giving a sense of discomfort or aversion to the subject or the measurer compared with the raw data of the face of the subject at the time when visible light is emitted thereto. For example, in the raw data of the face of the subject at the time when the infrared light is emitted thereto, the pupil is displayed in white, a blood vessel is displayed in a projected manner, or a beard is displayed in black excessively, whereby it is highly likely to give a sense of discomfort or aversion to the subject.

In the present embodiment, the raw data of the face of the subject is subject to the image processing to generate the composite image 176M, and the generated composite image 176M is displayed on the display device 101. Accordingly, the subject or the measurer can adjust, while viewing the composite image 176M displayed on the display device 101, the position or the orientation of the face of the subject or the position or the orientation of the eyeglasses 170 without a sense of discomfort or aversion.

Moreover, when the line-of-sight detection device 100 is used in the infant medical examination, giving a sense of discomfort or aversion to the parent in addition to the subject and the measurer is suppressed.

Further, in the present embodiment, the eyeglasses reflection image 172M is generated from the raw data by the image processing including binarization. By the eyeglasses reflection image 172M being generated, a reflection state of the infrared light on the eyeglasses 170 is clearly grasped. Accordingly, the subject or the measurer can adjust the position or the orientation of the face of the subject or can adjust the position or the orientation of the eyeglasses 170 worn on the subject such that the reflection image 172 of the light source 103 and the eye of the subject do not overlap in the visual field area of the stereo camera device 102.

Further, in the present embodiment, the contour image 174M is generated from the raw data by the image processing including binarization and edge detection. As described above, the contour image 174M includes at least one of the contour image of the face of the subject, the contour image of the eyelid of the subject, the contour image of the pupil 112 of the subject, the contour image of the naris of the subject, the contour image of the mouth of the subject, and the contour image of the eyeglasses 170 worn on the face of the subject. Those contour images 174M are images from which the subject or the measurer can recognize or estimate the position of the eye of the subject when the subject or the measurer views the contour image 174M. For example, when the contour image of the face is displayed on the display device 101, the subject or the measurer can recognize or estimate the approximate position of the eye of the subject based on the contour image of the face. Likewise, for example, when the contour image of the naris or the contour image of the eyeglasses 170 is displayed on the display device 101, the subject or the measurer can recognize or estimate the approximate position of the eye of the subject based on the contour image of the naris or the contour image of the eyeglasses 170. Further, when the contour image of the pupil of the subject is displayed on the display device 101, the subject or the measurer can recognize the position of the eye of the subject. Since the display device 101 displays the contour image 174M from which the position of the eye of the subject can be recognized or estimated, the subject or the measurer can recognize the relative position of the eye and the reflection image 172 based on the contour image 174M and the eyeglasses reflection image 172M displayed on the display device 101, and can adjust the position or the orientation of the face of the subject or can adjust the position or the orientation of the eyeglasses 170 worn on the subject such that the reflection image 172 of the light source 103 and the eye of the subject do not overlap in the visual field area of the stereo camera device 102.

Further, in the present embodiment, the display controller 208 causes the display device 101 to display the contour image 174M and the eyeglasses reflection image 172M in different display forms within the composite image 176M. As described above, the display form includes at least one of luminance, color, lightness, and saturation.

Accordingly, the subject or the measurer can sufficiently distinguish the contour image 174M and the eyeglasses reflection image 172M.

Further, in the present embodiment, the display controller 208 causes the display device 101 to display the eyeglasses reflection image 172M with the luminance higher than that of the contour image 174M. Accordingly, the subject or the measurer can promptly recognize the eyeglasses reflection image 172M.

Furthermore, in the present embodiment, the first threshold value and the second threshold value higher than the first threshold value are predetermined with regard to the luminance, and the image processing unit 206 generates the eyeglasses reflection image 172M having the luminance equal to or higher than the second threshold value and the contour image 174M having the luminance lower than the first threshold value. The display controller 208 causes the display device 101 to display the eyeglasses reflection image 172M with the luminance equal to or higher than the second threshold value, and causes the display device 101 to display the contour image 174M with the luminance lower than the first threshold value. In the present embodiment, as an example, the luminance of the contour image 174M is adjusted to 50% in a case where the luminance of the eyeglasses reflection image 172M is taken as 100%. As a result, a difference between the luminance of the eyeglasses reflection image 172M and the luminance of the contour image 174M is sufficiently provided. The subject or the measurer can therefore sufficiently distinguish the contour image 174M and the eyeglasses reflection image 172M. Therefore, the subject or the measurer can smoothly perform adjustment such that, while viewing the composite image 176M displayed on the display device 101, the reflection image 172 of the light source 103 and the eye of the subject do not overlap in the visual field area of the stereo camera device 102.

Moreover, in the present embodiment, the distance data between the display screen 101S of the display device 101 and the face of the subject is displayed on the display device 101. In the present embodiment, the scale 190 and the indicator 192 are displayed on the display device 101 as the distance data. The distance data displayed on the display device 101 supports the subject or the measurer such that, in the line-of-sight detection process, the face of the subject is placed at the optimum position in the Z-axis direction. Accordingly, the subject or the measurer can place the face of the subject at the optimum distance relative to the display device 101 and the stereo camera device 102 while viewing the indicator 192 of the display device 101. For example, in a case where the focal position of the optical system of the stereo camera device 102 is fixed, it becomes difficult to accurately detect the pupil 112 and the corneal reflection image 113 in the line-of-sight detection process when the distance between the subject and the display device 101/the stereo camera device 102 is too short. Besides, when the distance between the subject and the display device 101/the stereo camera device 102 is too long, the image of the eye of the subject obtained by the stereo camera device 102 becomes small, whereby it becomes difficult to accurately detect the pupil 112 and the corneal reflection image 113 in the line-of-sight detection process. As the display device 101 displays the distance data, the subject or the measurer can place, while viewing the distance data displayed on the display device 101, the face of the subject at the optimum position in the Z-axis direction.

Further, in the present embodiment, the display controller 208 causes the display screen 101S of the display device 101 to display the guide line 180 with the fixed dimension and position on the display screen 101S. The guide line 180 displayed on the display device 101 supports the subject such that, in the line-of-sight detection process, the face of the subject is placed at the optimum position in the X-axis direction and the Y-axis direction. As a result, the subject or the measurer can place the face of the subject at the optimum position in the line-of-sight detection process based on the guide line 180.

Note that, in the present embodiment, the first threshold value and the second threshold value higher than the first threshold value are predetermined, the luminance of the eyeglasses reflection image 172M is equal to or higher than the second threshold value, and the luminance of the contour image 174M is lower than the first threshold value. One threshold value may be predetermined for the luminance, the luminance of the eyeglasses reflection image 172M may be equal to or higher than the threshold value, and the luminance of the contour image 174M may be lower than the threshold value.

Second Embodiment

A second embodiment will be described. In the following descriptions, constituent elements same as or similar to those in the above-described embodiment are denoted by the same reference signs, and the descriptions thereof will be simplified or omitted.

In the positioning support process according to the above-described embodiment, the exemplary case where the detection light is emitted from the light source 103 with a constant amount of light, the first threshold value for the luminance and the second threshold value higher than the first threshold value are predetermined, and the contour image 174M having the luminance lower than the first threshold value and the eyeglasses reflection image 172M having the luminance higher than the second threshold value are generated through the image processing have been described.

In the present embodiment, an exemplary case where an amount of light of detection light emitted from a light source 103 is adjusted, and a contour image 174M and an eyeglasses reflection image 172M are generated based on image data obtained by a stereo camera device 102 at the time when the detection light with the adjusted amount of light is emitted onto a face of a subject will be described.

In the present embodiment, an image processing unit 206 generates the contour image 174M and the eyeglasses reflection image 172M based on the image data of the face of the subject obtained by the stereo camera device 102 at the time when the light source 103 emits the detection light of a first amount of light and the image data of the face of the subject obtained by the stereo camera device 102 at the time when the light source 103 emits the detection light of a second amount of light larger than the first amount of light.

In the present embodiment, in a positioning support process, a first light source 103A emits the detection light of the first amount of light, and a second light source 103B emits the detection light of the second amount of light larger than the first amount of light. The first light source 103A and the second light source 103B alternately emit the detection light. A second camera 102B of the stereo camera device 102 obtains the image data of the face of the subject at the time when the first light source 103A emits the detection light, and a first camera 102A obtains the image data of the face of the subject at the time when the second light source 103B emits the detection light.

The amount of light of the detection light emitted from the light source 103 includes total luminous flux [lm] or luminosity [cd] indicating the total amount of light emitted from the light source 103. When the amount of light is large, illuminance of the detection light emitted onto the face of the subject increases. When the amount of light is small, the illuminance of the detection light emitted onto the face of the subject decreases.

Figure 23:
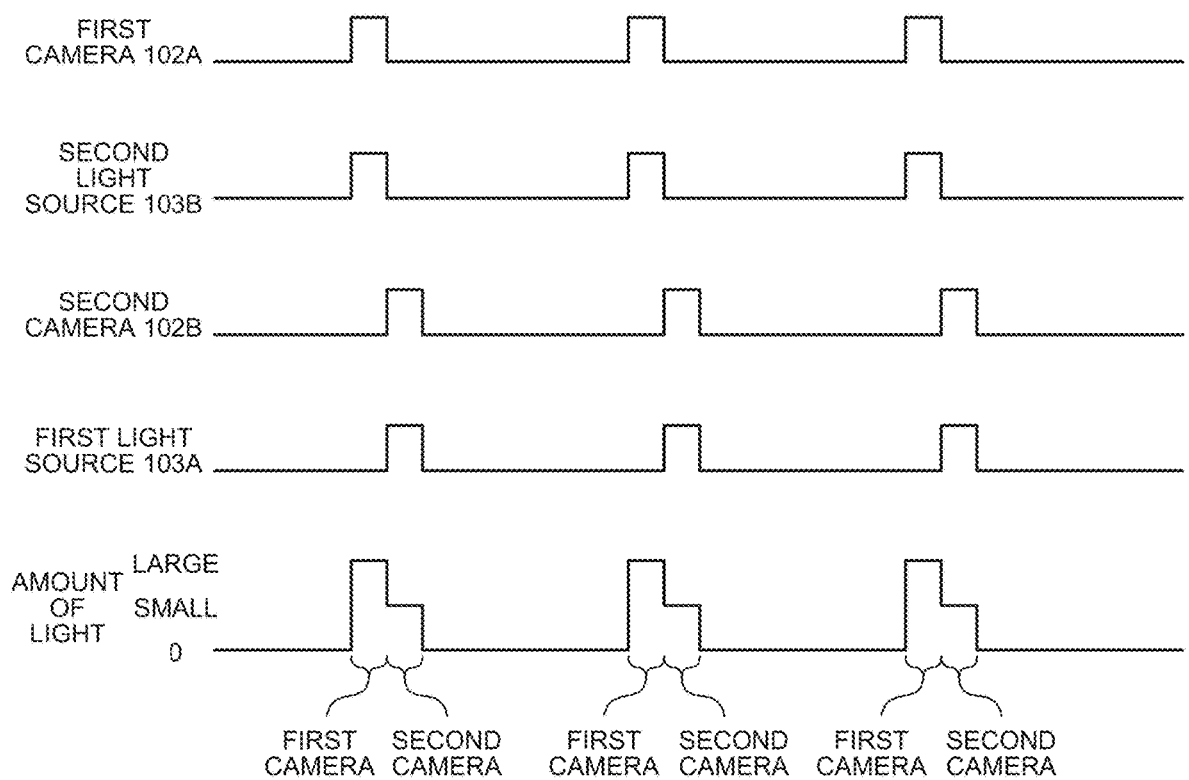
FIG. 23 is a timing chart illustrating an operation timing of a first camera, a second camera, a first light source, and a second light source in a positioning support process according to a second embodiment.

FIG. 23 is a timing chart illustrating an operation timing of the first camera 102A, the second camera 102B, the first light source 103A, and the second light source 103B in the positioning support process according to the present embodiment. As illustrated in FIG. 23, the first light source 103A and the second light source 103B alternately emit the detection light. The first camera 102A obtains the image data of the face of the subject in synchronization with the emission of the detection light from the second light source 103B. The second camera 102B obtains the image data of the face of the subject in synchronization with the emission of the detection light from the first light source 103A. The amount of light of the detection light emitted from the second light source 103B at the time when the first camera 102A obtains the image data is larger than the amount of light of the detection light emitted from the first light source 103A at the time when the second camera 102B obtains the image data.

In the present embodiment, when the first camera 102A operates, in other words, when the shutter of the first camera 102A opens, light enters the imaging element of the first camera 102A. The light entering the imaging element is converted into an electric signal. The electric signal is converted into a universal serial bus (USB) signal, and then transferred to a computer system 20 to activate the second light source 103B. That is, at the timing when the shutter of the first camera 102A opens, the detection light is emitted from the second light source 103B corresponding to the first camera 102A. The same applies to the second camera 102B and the first light source 103A.

Note that, in the present embodiment, in order to detect a dark pupil, the detection light is emitted from, among the first light source 103A and the second light source 103B, the second light source 103B disposed at a position away from the first camera 102A when the first camera 102A operates, and the detection light is emitted from, among the first light source 103A and the second light source 103B, the first light source 103A disposed at a position away from the second camera 102B when the second camera 102B operates. Note that, in a case of detecting a bright pupil, the detection light is emitted from, among the first light source 103A and the second light source 103B, the first light source 103A disposed at a position close to the first camera 102A when the first camera 102A operates, and the detection light is emitted from, among the first light source 103A and the second light source 103B, the second light source 103B disposed at a position close to the second camera 102B when the second camera 102B operates.

Note that time required for the second camera 102B and the first light source 103A to operate after the first camera 102A and the second light source 103B operate is short, and time required for the first camera 102A and the second light source 103B to operate after the second camera 102B and the first light source 103A operate is long. Since the time required for the second camera 102B and the first light source 103A to operate after the first camera 102A and the second light source 103B operate is short, right and left stereo images can be obtained at approximately the same timing.

In the present embodiment, in the positioning support process, the contour image 174M is generated based on the image data obtained by the first camera 102A, and the eyeglasses reflection image 172M is generated based on the image data obtained by the second camera 102B. In other words, the contour image 174M is generated based on the image data of the face of the subject irradiated with the detection light of a large amount of light emitted from the second light source 103B, and the eyeglasses reflection image 172M is generated based on the image data of the face of the subject irradiated with the detection light of a small amount of light emitted from the first light source 103A.

When the first camera 102A obtains the image data of the face of the subject, the face of the subject is illuminated with the detection light of a large amount of light. Therefore, when the image data obtained by the first camera 102A is binarized based on a predetermined threshold value, for example, as illustrated in FIG. 13, most of a plurality of pixels of the binarized image data is converted into white color. That is, not only eyeglasses 170 but also the entire face of the subject is converted into white color. Edge detection is performed on the binarized image data, thereby generating the contour image 174M.

On the other hand, when the second camera 102B obtains the image data of the face of the subject, the face of the subject is illuminated with the detection light of a small amount of light. Therefore, when the image data obtained by the second camera 102B is binarized based on the predetermined threshold value, for example, as illustrated in FIG. 16, among a plurality of pixels of the binarized image data, only pixels corresponding to a reflection image 172 are converted into white color, and pixels corresponding to the face of the subject are converted into black color. That is, the image data of the face of the subject illuminated with the detection light of a small amount of light is binarized, thereby generating the eyeglasses reflection image 172M.

Figure 24:
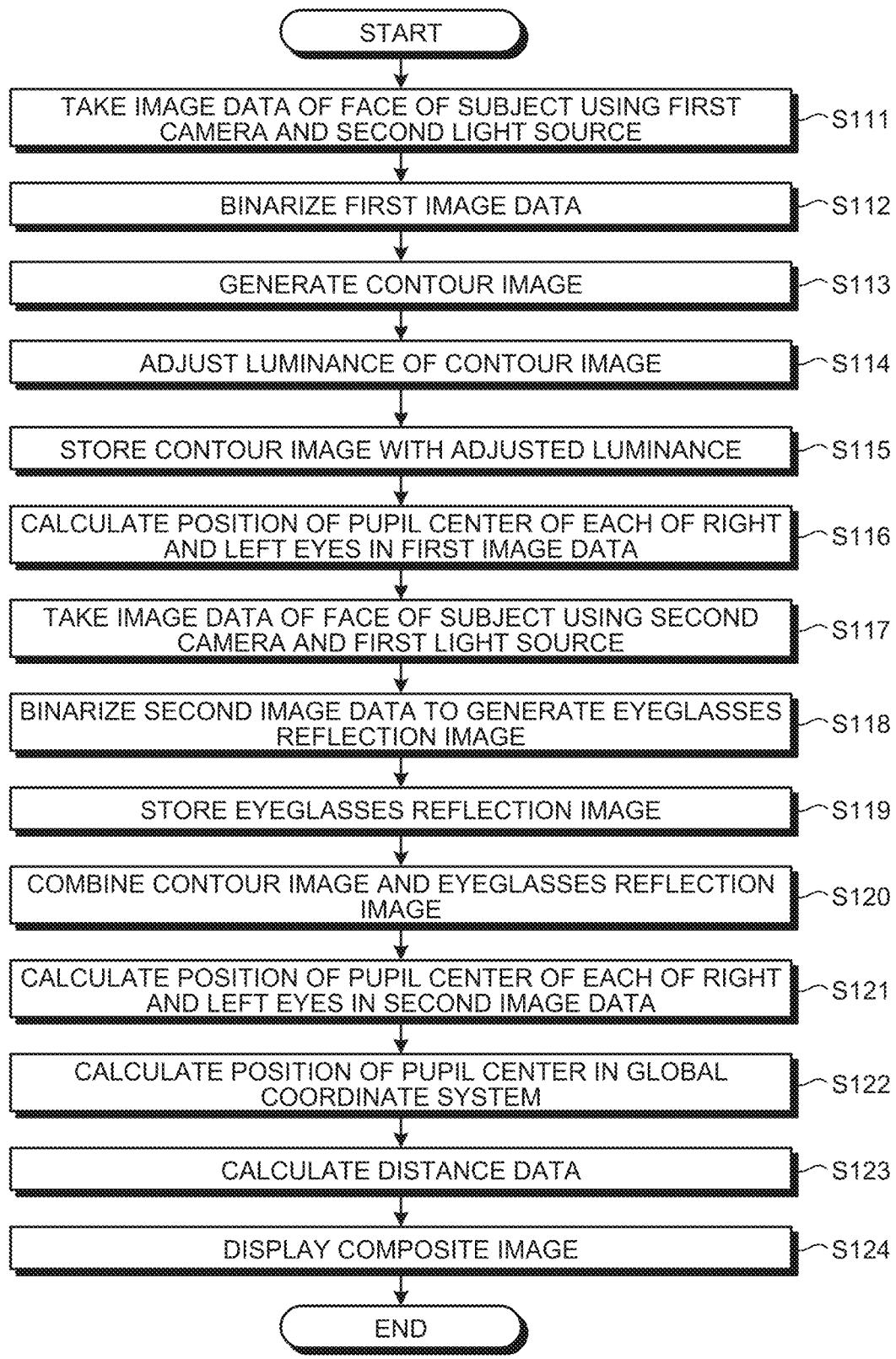
FIG. 24 is a flowchart illustrating an example of the positioning support process according to the second embodiment.

FIG. 24 is a flowchart illustrating an exemplary positioning support process according to the present embodiment.

The light source controller 210 causes the second light source 103B to emit the detection light of a large amount of light. The image data of the face of the subject illuminated with the detection light of the large amount of light is obtained by the first camera 102A (step S111).

The image data acquisition unit 202 acquires the image data from the first camera 102A. The image processing unit 206 binarizes first image data, which is the image data obtained by the first camera 102A, based on the predetermined threshold value (step S112). As a result, the image data as illustrated in FIG. 13 is generated.

The image processing unit 206 performs the edge detection on the binarized first image data. As a result, the contour image 174M as illustrated in FIG. 14 is generated (step S113).

Next, the image processing unit 206 adjusts the luminance of the contour image 174M (step S114). The image processing unit 206 reduces the luminance of the contour image 174M. As a result, the contour image 174M as illustrated in FIG. 15 is generated.

The contour image 174M having been subject to the luminance adjustment is stored in the storage 220 (step S115).

Next, the position detection unit 212 calculates the position of the pupil center 112C of each of the right and left eyes in the first image data (step S116).

Next, the light source controller 210 causes the first light source 103A to emit the detection light of a small amount of light. The image data of the face of the subject illuminated with the detection light of the small amount of light is obtained by the second camera 102B (step S117).

The image data acquisition unit 202 acquires the image data from the second camera 102B. The image processing unit 206 binarizes second image data, which is the image data obtained by the second camera 102B, based on the predetermined threshold value (step S118). As a result, the image data as illustrated in FIG. 16 is generated. That is, the second image data is binarized, thereby generating the eyeglasses reflection image 172M.

In the present embodiment, the same value is used as the threshold value for binarizing the second image data used in step S118 and the threshold value for binarizing the first image data used in the step S112.

The generated eyeglasses reflection image 172M is stored in the storage 220 (step S119).

Next, the image processing unit 206 combines the contour image 174M and the eyeglasses reflection image 172M stored in the storage 220 (step S120). As a result, the composite image 176M as illustrated in FIG. 17 is generated.

Next, the position detection unit 212 calculates the position of the pupil center 112C of each of the right and left eyes in the second image data (step S121).

Next, the curvature center calculation unit 214 calculates the position of the pupil center 112C in the global coordinate system based on at least one of the positional data of the pupil center 112C calculated based on the first image data in step S116 and the positional data of the pupil center 112C calculated based on the second image data in step S121 (step S122).

Next, the distance data acquisition unit 218 calculates distance data between the display screen 101S of the display device 101 and the face of the subject based on the positional data of the pupil center 112C calculated in step S122 (step S123).

The display controller 208 causes the display device 101 to display the composite image 176M generated in step S120 (step S124). Further, the display controller 208 causes the display device 101 to display the distance data calculated in step S123. In a similar manner to the above-described embodiment, the display controller 208 causes the display device 101 to display the scale 190 and the indicator 192 as the distance data.

Note that, in the positioning support process, it is only necessary to obtain approximate distance data between the display screen 101S of the display device 101 and the face of the subject. Therefore, in step S122, the distance data between the display screen 101S of the display device 101 and the face of the subject may be calculated based on, among the positional data of the pupil center 112C of the right and left eyes, the positional data of the pupil center 112C of either one of the eyes. Alternatively, the distance data between the display screen 101S of the display device 101 and the face of the subject may be calculated based on an average value of the positional data of the pupil center 112C of the right and left eyes.

As described above, according to the present embodiment, the amount of light of the detection light emitted from the light source 103 is changed in the positioning support process. Thus, only one threshold value suffices as a threshold value for the luminance used in the image processing. A computer program 20C for controlling a line-of-sight detection device 100 is therefore simplified. For example, by merely changing the amount of light of the light source 103 in the positioning process, no big difference between contents of the computer program 20C used in the positioning support process and contents of the computer program 20C used in the line-of-sight detection process is needed.

Note that, in the present embodiment, the contour image 174M and the eyeglasses reflection image 172M are obtained by controlling the amount of light of the detection light emitted from the light source 103. That is, when the image data of the face of the subject is obtained by the first camera 102A, the face of the subject is illuminated with the detection light of a large amount of light to generate the contour image 174M based on the image data of the face of the subject illuminated with the detection light of the large amount of light, and when the image data of the face of the subject is obtained by the second camera 102B, the face of the subject is illuminated with the detection light of a small amount of light to generate the eyeglasses reflection image 172M based on the image data of the face of the subject illuminated with the detection light of the small amount of light. When the image data acquisition unit 202 obtains the image data of the face of the subject from the first and second cameras 102A and 102B that take the image of the face of the subject illuminated with the detection light, the image processing unit 206 may generate the contour image 174M and the eyeglasses reflection image 172M based on the image data of the subject's face, obtained by the first and second cameras 102A and 102B and acquired by the image data acquisition unit 202, of a first exposure amount and the image data of the subject's face of a second exposure amount smaller than the first exposure amount.

The exposure amount of the image data of the subject's face obtained by the first and second cameras 102A and 102B can be adjusted based on at least one of light emission intensity of the light source 103, light emission time of the light source 103, and an exposure value of the first and second cameras 102A and 102B. As described above, the light source controller 210 can control the light emission intensity of the first and second light sources 103A and 103B and the light emission time of the first and second light sources 103A and 103B. A camera controller 211 can control the exposure value in the imaging element by controlling at least one of a shutter speed and an aperture value of the optical system of the first and second cameras 102A and 102B.

When the first camera 102A obtains the image data of the face of the subject, the light source controller 210 may increase the light emission intensity of the second light source 103B, the light source controller 210 may increase the light emission time of the second light source 103B, the camera controller 211 may reduce the shutter speed of the first camera 102A, and the camera controller 211 may reduce the aperture value of the optical system of the first camera 102A to increase the exposure amount of the image data of the subject's face obtained by the first camera 102A, and thus the image processing unit 206 may generate the contour image 174M based on the image data of the face of the subject having a large exposure amount. Further, when the second camera 102B obtains the image data of the face of the subject, the light source controller 210 may reduce the light emission intensity of the first light source 103A, the light source controller 210 may reduce the light emission time of the first light source 103A, the camera controller 211 may increase the shutter speed of the second camera 102B, and the camera controller 211 may increase the aperture value of the optical system of the second camera 102B to reduce the exposure amount of the image data of the subject's face obtained by the second camera 102B, and thus the image processing unit 206 may generate the eyeglasses reflection image 172M based on the image data of the face of the subject having a small exposure amount.

Note that, in the present embodiment, the contour image 174M is generated from the first image data obtained by the first camera 102A, and the eyeglasses reflection image 172M is generated from the second image data obtained by the second camera 102B. Although the contour image 174M and the eyeglasses reflection image 172M are generated from separate image data, the composite image 176M having sufficient accuracy is generated from the viewpoint of supporting positioning.

Note that, in the embodiment described above, a lens of the eyeglasses 170 may be a prescription lens having eyesight adjustment function, or may be a lens having no eyesight adjustment function. Besides, the eyeglasses 170 may or may not have a light shielding function. In the present embodiment, the eyeglasses 170 include sunglasses.

Further, the eyeglasses 170 may not be worn on the face of the subject. In the present embodiment, the eyeglasses 170 is a concept including an optical member having a light transmission function disposed between the line-of-sight detection device 100 and the eye of the subject.

Note that, in the embodiment described above, the eyeglasses reflection image 172M has the luminance higher than that of the contour image 174M. The luminance of the eyeglasses reflection image 172M may be the same as the luminance of the contour image 174M, or may be lower than the luminance of the contour image 174M. In a case where the luminance of the eyeglasses reflection image 172M and the luminance of the contour image 174M are approximated, the eyeglasses reflection image 172M and the contour image 174M are preferably displayed in different colors.

Note that, in the embodiment described above, the feature image of the face of the subject is the contour image generated by the edge detection. The feature image only needs to be an image from which the position of the eye of the subject can be recognized or estimated when the subject or the measurer views the feature image, and may not be the contour image obtained by the edge detection.

The present embodiments are suitable for performing detection of a line of sight of a subject wearing eyeglasses.

According to the present embodiments, there are provided a line-of-sight detection device and a method for detecting a line of sight capable of suppressing deterioration of detection accuracy of a line of sight of a subject wearing eyeglasses.

Although the application has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A line-of-sight detection device, comprising:
    an image data acquisition unit configured to acquire image data of a face of a subject irradiated with detection light emitted from at least one light source;
    a line-of-sight detection unit configured to detect a line of sight of the subject based on the image data;
    an image processing unit configured to perform image processing on the image data to separately generate a feature image of the face and an eyeglasses reflection image indicating a reflection image of the at least one light source on eyeglasses worn on the face; and
    a display controller configured to cause a display device to display the feature image and the eyeglasses reflection image in a different display form in a composite image in which the feature image and the eyeglasses reflection image are combined, wherein
    the image processing unit is further configured to generate the feature image and the eyeglasses reflection image based on the image data obtained at a time when the detection light of a first amount of light is emitted from the at least one light source and the image data obtained at a time when the detection light of a second amount of light larger than the first amount of light is emitted from the at least one light source,
    the at least one light source includes a first light source and a second light source disposed at a different position,
    the detection light of the first amount of light is emitted from the first light source, and the detection light of the second amount of light is emitted from the second light source, and
    the first light source and the second light source alternately emit the detection light.

2. The line-of-sight detection device according to claim 1, wherein
    the display form includes at least one of luminance, color, lightness, and saturation, and the feature image includes a contour image of the face.

3. The line-of-sight detection device according to claim 1, wherein
    the display controller is configured to cause the display device to display the eyeglasses reflection image with luminance higher than luminance of the feature image.

4. The line-of-sight detection device according to claim 1, wherein
    a first threshold value and a second threshold value higher than the first threshold value are predetermined, and
the image processing unit is configured to generate
    the eyeglasses reflection image with luminance equal to or higher than the second threshold value, and generates the feature image with luminance equal to or lower than the first threshold value.

5. The line-of-sight detection device according to claim 1, wherein
    the image data acquisition unit is configured to acquire the image data from at least one camera that takes an image of the face illuminated with the detection light, and
    the image processing unit is configured to generate the feature image and the eyeglasses reflection image based on the image data of a first exposure amount obtained by the at least one camera and image data of a second exposure amount smaller than the first exposure amount obtained by the at least one camera.

6. The line-of-sight detection device according to claim 5, further comprising:
    a light source controller configured to control light emission intensity of the at least one light source and light emission time of the at least one light source; and
    a camera controller configured to control an exposure value of the detection light in the at least one camera, wherein
    the exposure amount of the image data is adjusted based on at least one of the light emission intensity of the at least one light source, the light emission time of the at least one light source, and the exposure value of the at least one camera.

7. The line-of-sight detection device according to claim 1, further comprising:
    a distance data acquisition unit configured to acquire distance data between a display screen of the display device and the face, wherein
    the display controller is configured to cause the display device to display the distance data.

8. The line-of-sight detection device according to claim 1, wherein
    the display controller is configured to cause the display device to display a guide line with a fixed dimension and position on the display screen of the display device.

9. A method for detecting a line of sight, comprising:
    acquiring image data of a face of a subject irradiated with detection light emitted from at least one light source;
    generating separately, by performing image processing on the image data, a feature image of the face and an eyeglasses reflection image indicating a reflection image of the at least one light source on eyeglasses worn on the face;
    causing a display device to display the feature image and the eyeglasses reflection image in a different display form in a composite image in which the feature image and the eyeglasses reflection image are combined; and
    detecting a line of sight of the subject based on the image data, wherein
    the feature image and the eyeglasses reflection image are generated based on the image data obtained at a time when the detection light of a first amount of light is emitted from the at least one light source and the image data obtained at a time when the detection light of a second amount of light larger than the first amount of light is emitted from the at least one light source,
    the at least one light source includes a first light source and a second light source disposed at a different position,
    the detection light of the first amount of light is emitted from the first light source, and the detection light of the second amount of light is emitted from the second light source, and
    the first light source and the second light source alternately emit the detection light.

* * * * *